United States Patent [19]

Carson

[11] 3,952,012

[45] Apr. 20, 1976

[54] AROYL-SUBSTITUTED PYRROLES

[75] Inventor: John Robert Carson, Norristown, Pa.

[73] Assignee: McNeil Laboratories, Incorporated, Fort Washington, Pa.

[22] Filed: June 17, 1974

[21] Appl. No.: 491,965

Related U.S. Application Data

[60] Division of Ser. No. 338,461, Feb. 16, 1973, Pat. No. 3,865,840, which is a division of Ser. No. 5,958, Jan. 26, 1970, Pat. No. 3,752,826, which is a continuation-in-part of Ser. No. 741,348, July 1, 1968, abandoned, which is a continuation-in-part of Ser. No. 656,074, July 26, 1967, abandoned.

[52] U.S. Cl............... 260/326.47; 260/326.46; 424/274

[51] Int. Cl.$^2$................ C07D 207/24

[58] Field of Search.............. 260/326.47, 326.46

[56] References Cited

FOREIGN PATENTS OR APPLICATIONS 42-10509   7/1967   Japan.................... 326/46

*Primary Examiner*—Frederick E. Waddell
*Attorney, Agent, or Firm*—Salvatore R. Conte

[57] ABSTRACT

The compounds are of the class of 5-aroyl-pyrrole alkanoic acids and corresponding acid derivatives thereof useful as anti-inflammatory agents and as synthetic intermediates.

2 Claims, No Drawings

AROYL-SUBSTITUTED PYRROLES

This is a divisional application of my copending application Ser. No. 338,461, filed Feb. 16, 1973, issued as U.S. Pat. No. 3,865,840 on Feb. 11, 1975, which in turn is a divisional application of application Ser. No. 5,958, filed Jan. 26, 1970, issued as U.S. Pat. No. 3,752,826 on Aug. 14, 1973, which in turn is a continuation-in-part application of application Ser. No. 741,348, filed July 1, 1968, now abandoned, which in turn is a continuation-in-part application of application Ser. No. 656,074, filed July 26, 1967, now abandoned.

This invention relates to novel 5-aroyl-pyrroles, and, more particularly, to 5-aroyl-pyrrole alkanoic acids and the corresponding salts, esters, nitriles, amides and substituted amides thereof. Said 5-aroyl-pyrroles may be represented by the following formulas:

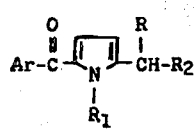 (I-a),

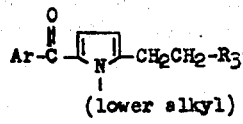 (I-b),

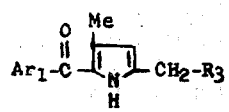 (I-c),

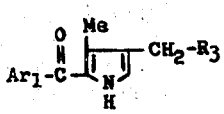 (I-d), and 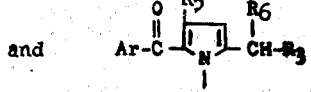 (I-e)

wherein:

Ar represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano and methylthio;

$Ar_1$ represents a member selected from the group consisting of phenyl, monosubstituted phenyl and polysubstituted phenyl, each substituent of said substituted phenyls being a member selected from the group consisting of halo, lower alkyl and lower alkoxy;

R represents a member selected from the group consisting of hydrogen and lower alkyl;

$R_1$ represents a member selected from the group consisting of hydrogen, lower alkyl and benzyl;

$R_2$ represents a member selected from the group consisting of CN, COOH, COO-(lower alkyl), $CONH_2$, CONH—(lower alkyl), CON-(lower alkyl)$_2$, CONH-OH and CONH-$(CH_2)_n$-N(lower alkyl), in which n is an integer of from 2 to 4 carbon atoms;

$R_3$ represents a member selected from the group consisting of COOH, COO-(lower alkyl), $CONH_2$, CONH-(lower alkyl) and CON-(lower alkyl)$_2$;

$R_4$ represents lower alkyl;

$R_5$ represents lower alkyl; and $R_6$ represents a member selected from the group consisting of hydrogen and lower alkyl;

provided that:

i. when said Ar is a member selected from the group consisting of nitro-substituted phenyl and amino-substituted phenyl, then, with regard to Formula (I-a), said R is hydrogen, said $R_1$ is lower alkyl and said $R_2$ is a member selected from the group consisting of CN, COOH and COO-(lower alkyl); and with regard to Formula (I-e), said $R_6$ is hydrogen;

ii. when said Ar is cyanophenyl, then said $R_1$ is lower alkyl and said $R_2$ is a member selected from the group consisting of COOH and COO-(lower alkyl); and iii. when said $R_1$ is hydrogen, then said R is hydrogen.

The non-toxic, therapeutically acceptable salts of such acids, such as are obtained from appropriate organic or inorganic bases, are also embraced within the scope of this invention.

As used herein, "lower alkyl" and "lower alkoxy" may be straight or branch chained saturated hydrocarbons having from 1 to about 6 carbon atoms, such as, for example, methyl, ethyl, propyl, isopropyl, butyl, pentyl, hexyl and the like alkyls, and, respectively, the corresponding alkoxys such as methoxy, ethoxy, propoxy, isopropoxy, etc.

The subject compounds may be obtained by means of several synthetic processes. For example, the compounds of formula (I-a), in which $R_2$ is CN or COO-(lower alkyl), are generally prepared by a Friedel-Crafts reaction between an appropriate aroyl halide, preferably the chloride (II), and a pyrrole-2-acetic acid derivative of formula (III), wherein R' is cyano or lower alkoxycarbonyl in the presence of a Lewis acid, preferably a metallic halide such as aluminum chloride. Suitable solvents are those typically employed in a Friedel-Crafts reaction, such as, for example, methylene chloride, 1,2-dichloroethane, carbon disulfide, nitrobenzene and the like. The acid derivative (IV) thus obtained can then be converted to the corresponding free carboxylic acid by conventional hydrolysis, for example, by heating a solution of (IV) in aqueous methanol with an alkali metal hydroxide to form the alkali metal salt of the acid and then acidifying the mixture. The foregoing reactions may be illustrated by the following schematic diagram.

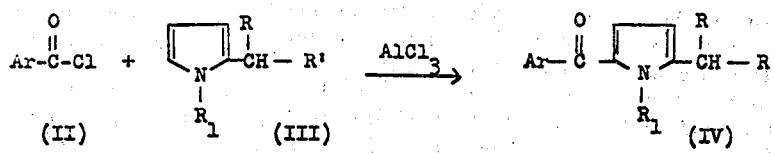

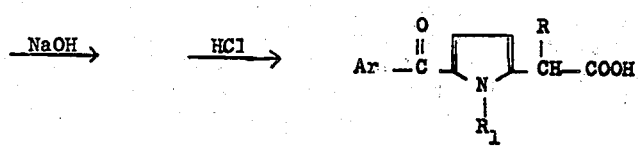

The aroyl chlorides (II) are generally known and may be obtained by transformation of the corresponding acid to the acid chloride form according to conventional procedures, such as, for example, the procedure hereinafter demonstrated in Example LXXXI.

Alternatively, to prepare the nitriles, esters and acids of formula (I-a), wherein R is lower alkyl, a 5-aroyl-pyrrole-2-acetic acid derivative of the formula:

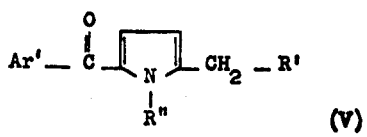

wherein R' is as previously described, R'' is lower alkyl or benzyl, and Ar' is thienyl, 5-methylthienyl, phenyl or phenyl substituted with halo, lower alkyl, trifluoromethyl, methylthio, lower alkoxy or cyano, which acid derivative (V) may be obtained in accordance with the aforementioned Friedel-Crafts procedure, is alkylated according to conventional alkylation techniques, e.g., with a lower alkyl halide as the alkylating agent in the presence of a strong base such as sodium amide or sodium hydride, to yield the corresponding nitriles and esters:

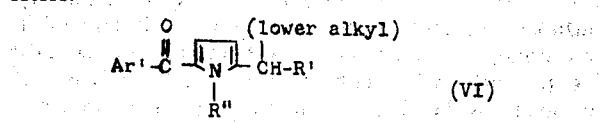

from which the corresponding acids are obtained by conventional hydrolysis.

The acetonitriles of formula (VI), in which R'' is lower alkyl, are also obtained by conventional N-alkylation of an N-unsubstituted 5-aroyl-pyrrole-2-acetonitrile of the formula:

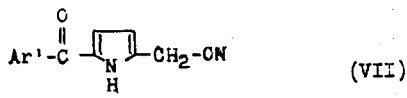

followed by conventional C-alkylation of the thus-obtained N-alkyl-5-aroyl-pyrrole-2-acetonitrile using an appropriate lower alkyl halide as the alkylating agent in each step. After the N-alkylation step or the C-alkylation step, corresponding acids may be obtained by conventional hydrolysis.

The nitriles, esters and acids of formula (I-a), wherein Ar is amino-substituted phenyl, are preferably prepared from the corresponding 5-nitrobenzoyl-1-(lower alkyl)-pyrrole-2-acetic acid esters or nitriles according to the following reaction scheme in which the corresponding para-derivatives are exemplified (R' being as previously described):

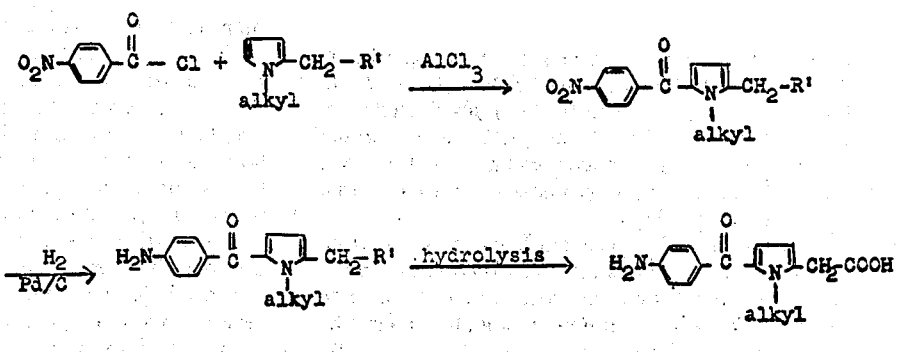

In the foregoing reaction sequence, the nitro function of the 5-nitrobenzoyl-1-(lower alkyl)-pyrrole-2-acetic acid ester or nitrile (obtained by the Friedel-Crafts type of reaction previously described) is catalytically hydrogenated, for example, with hydrogen and palladium-on-carbon catalyst, to yield the corresponding 5-aminobenzoyl-1-(lower alkyl)-pyrrole-2-acetic acid ester or nitrile which is then hydrolyzed to the corresponding free acid form.

Esterification of the acids of formula (I-a) with a slight excess of an appropriate lower alkanol yields the corresponding esters, i.e., wherein $R_2$ equals COO- (lower alkyl). Preferably, the methyl esters of formula (I-a) are obtained by the Friedel-Crafts reaction previously described between an appropriate aroyl halide (II) and an appropriate methyl pyrrole-2-acetate (III).

The primary amides of formula (I-a) are readily obtained by partial hydrolysis of the corresponding nitriles of formula (I-a). The nitrile-to-amide transformation is accomplished according to conventional procedures, for example, by treatment of the nitrile with aqueous sodium hydroxide under reflux for a relatively short time, that is, a period sufficient for partial hydrolysis to the amide stage as opposed to complete hydrolysis to the carboxylic acid stage. The corresponding lower alkyl-substituted amides are preferably obtained by first transforming the carboxylic function of the formula (I-a) acids into the corresponding acid chloride form, for example, by treatment of the acid or its alkali metal salt with thionyl chloride or oxalyl chloride, and then reacting the thus-obtained acid chloride with an appropriate lower alkyl-amine or di-(lower alkyl)-amine to yield the corresponding N-alkyl or N,N-dialkyl amides, respectively, of formula (I-a). Alternatively, the amides of formula (I-a) may be obtained by conventional ammonolysis of the corresponding lower alkyl esters employing ammonia, or, to prepare the substituted amides of formula (I-b), by employing an appropriately substituted amine, such as, for example, a primary lower alkylamine, a secondary lower alkylamine, an amine of the formula $H_2N-(CH_2)_n-H-$(lower alkyl)$_2$ in which $n$ is the integer 2, 3 or 4, or hydroxylamine (preferably as the hydrochloride), preferably in an alcoholic solvent at elevated temperatures and in the presence of a basic catalyst normally employed in such ester to amide transformations, e.g., sodium methoxide.

The compounds of formula (I-b), wherein $R_3$ is COO-(lower alkyl), preferably ethoxycarbonyl, and Ar is other than aminophenyl are prepared by a Friedel-Crafts reaction between an appropriate aroyl halide, preferably the chloride (VIII), and a lower alkyl 1-(lower alkyl)-pyrrole-2-propionate (IX). Conventional hydrolysis of the thus-obtained lower alkyl 5-aroyl-1-(lower alkyl)-pyrrole-2-proprionate (X) yields the corresponding free acids of formula (I-b). In turn, the esters and acids may be converted to the corresponding amides of formula (I-b) according to conventional procedures as previously described for formula (I-a) using ammonia, or an appropriate alkyl or dialkyl amine.

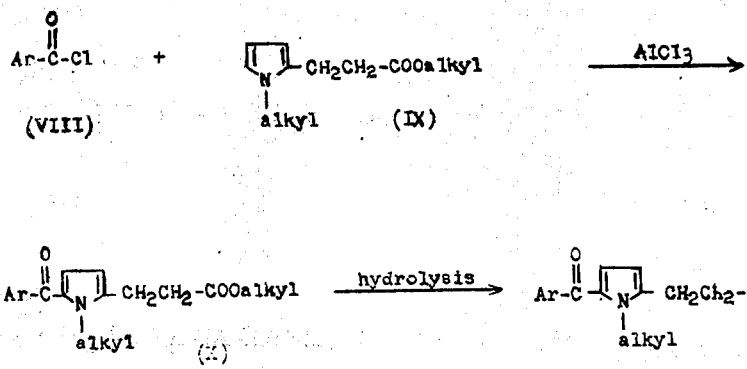

The formula (I-b) compounds, wherein Ar is aminophenyl, are preferably obtained from the corresponding lower alkyl 5-nitrobenzoyl-1-(lower alkyl)-pyrrole-2-propionate (obtained by the usual Friedel-Crafts type of reaction between nitrobenzoyl chloride and alkyl propionate (IX) by transforming the nitro function to an amino function according to the reaction scheme previously described for the formula (I-a) compounds, i.e., by means of catalytic hydrogenation followed by hydrolysis.

The alkyl propionates (IX) may be prepared by first treating an appropriate N-alkylpyrrole-2-carboxaldehyde with an appropriate alkoxycarbonyl-methylene triphenylphosphorane [see R. Jones et al., Canad. Jour. Chem., 18, 883 (1965)] and then hydrogenating the thus-obtained alkyl 2-(1-alkyl-2-pyrrolyl)-acrylate, thereby saturating the double bond of the acrylate function, to yield the desired alkyl propionate (IX).

The compounds of formula (I-c), wherein $R_4$ is hydrogen, are prepared from an appropriate 1-aryl-1,2,3-butanetrione-2-oxime (XI) and an appropriate dialkyl acetonedicarboxylate (XII) as starting materials. The two are contacted together according to a Knorr pyrrole synthesis in glacial acetic acid in the presence of zinc dust to yield the ring-closed pyrrole, alkyl 5-aroyl-3-alkoxycarbonyl-4-methylpyrrole-2-acetate (XIII). Hydrolysis of the latter with moderately concentrated alkali, for example 25–50% aqueous sodium hydroxide gives the corresponding free di-acid (XIV) which is then partially reesterified using an acidic solution of a lower alkanol to yield the corresponding alkyl 5-aroyl-3-carboxy-4-methylpyrrole-2-acetate (XV). Decarboxylation of the carboxy group in the 3-position is then accomplished by heating the latter in a suitable basic organic solvent such as quinoline. The resulting alkyl 5-aroyl-4-methylpyrrole-2-acetate (XVI) is then hydrolyzed in the usual manner to give the desired free acids (XVXI) of formula (Ic). In turn, the acids may be esterified using lower alkanols to the corresponding lower alkyl esters of formula (I-c) and such acids or esters are converted to the corresponding amides of formula (I-c) according to conventional procedures using ammonia, or an appropriate alkyl or dialkyl amine. The foregoing reaction sequence may be illustrated by the following diagrammatic scheme:

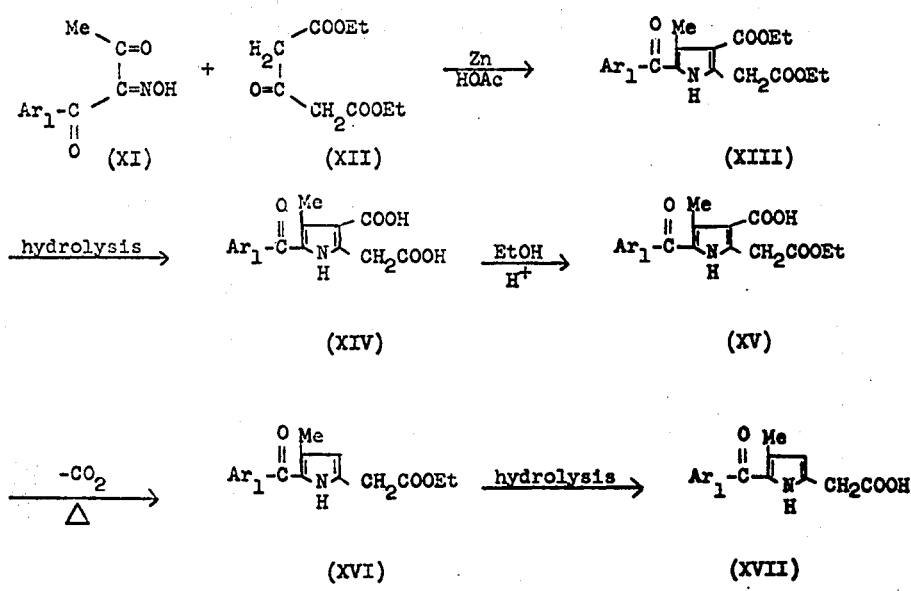

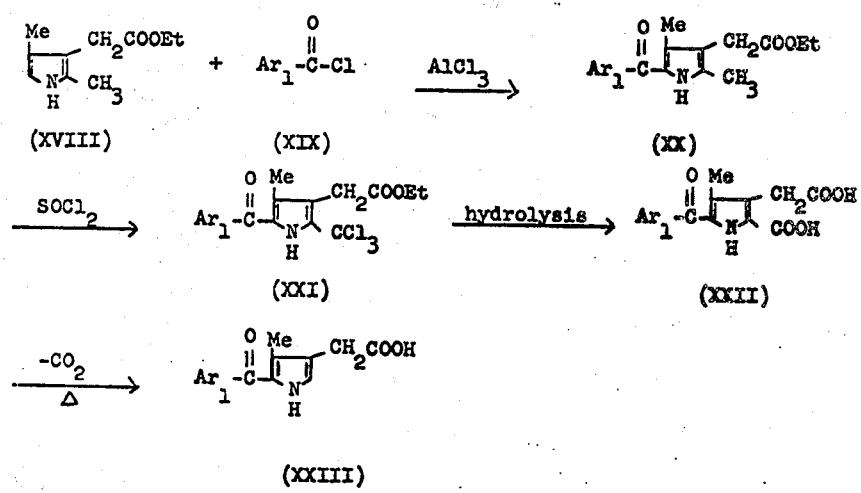

The compounds of formula (I-d) are prepared from the known pyrrole ester, ethyl 2,4-dimethylpyrrole-3-acetate (XVIII), which is acylated according to a Friedel-Crafts reaction using an appropriate benzoyl halide, preferably the chloride (XIX), as the acylating agent. The methyl group in the 2-position of the thus-obtained ethyl 5-benzoyl-2,4-dimethylpyrrole-3-acetate (XX) is then perchlorinated by treating said ester (XX) with sulfuryl chloride in an inert solvent such as ether to yield the corresponding ethyl 5-benzoyl-4-methyl-2-trichloromethylpyrrole-2-acetate (XXI). Hydrolysis of the latter, for example, by heating at reflux in aqueous dioxane or 1,2-dimethoxyethane, for a few hours, gives the di-acid, 5-benzoyl-4-methyl-2-carboxypyrrole-3-acetic acid (XXII). The carboxy function on the 2-position is then removed, for example, by heating in a suitable basic organic solvent such as qunioline to yield the desired free acids (XXIII) of formula (I-d). Again, the acids may in turn be converted to the corresponding esters, from which acids and esters the amides of formula (I-d) are produced in the usual manner. The foregoing reaction sequence may be illustrated by the following diagrammatic scheme:

The compounds of formula (I-c), wherein $R_6$ is hydrogen, are prepared according to the following synthetic sequence. An appropriate chloromethyl loweralkyl ketone of formula XXIV is added to a mixture of an appropriate di-loweralkyl acetone dicarboxylate, preferably the diethyl ester (XII), and a loweralkylamine ($R_4$—$NH_2$), preferably in an aqueous medium. The reaction temperature is preferably maintained just below 60°C. and, after a few hours, the mixture is treated witch ice-hydrochloric acid. The thus-obtained ring-closed pyrrole, alkyl 1-loweralkyl)-4-loweralkyl-3-alkoxycarbonyl-pyrrole-2-acetate (XXV) in then acylated with an appropriate aroyl halide, preferably the chloride, of the formula: Ar—COCl wherein Ar is as previously described, except for phenyl substituted with lower alkoxy, amino, cyano and methylthio, under Friedel-Crafts reaction conditions to yield the corresponding alkyl 5-aroyl-1-loweralkyl-4-loweralkyl-3-alkoxycarbonyl-pyrrole-2-acetate (XXVI). The foregoing reaction scheme may be illustrated as follows (the symbols "$R_4$" and "$R_5$" being as previously described):

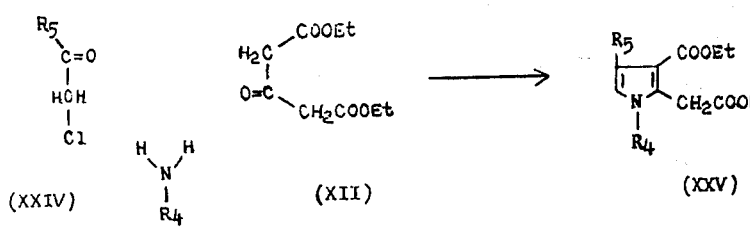

(XXIV)    (XII)    (XXV)

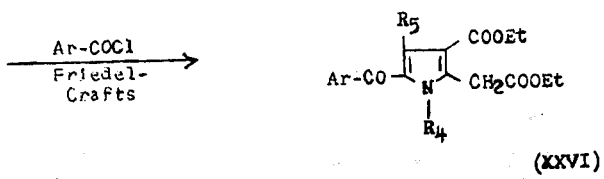

(XXVI)

The thus-obtained 5-acyl product (XXVI) is then subjected to the same synthetic sequence as previously described for product (XIII), namely, the successive steps of hydrolysis, partial re-esterification, decarboxylation and hydrolysis to give the 1-$R_4$-4-$R_5$-5-acyl derivatives corresponding to prodcts (XIV) through (XVII), respectively:

which is then partially re-esterified using an acidic solution of a lower alkanol to yield the corresponding lower alkyl 1-$R_4$-4-$R_5$-3-carboxypyrrole-2-acetate (XXXII), the 3-position of which is then decarboxylated, for example, by heating in an inert atmosphere until gas evolution ceases or by heating in a suitable basic organic solvent such as quinoline, and the thus-obtained lower alkyl 1-$R_4$-4-$R_5$-pyrrole-2-acetate

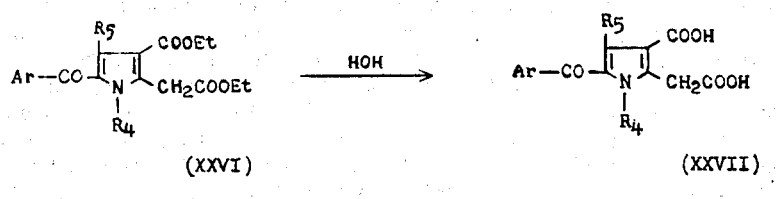

(XXVI)    (XXVII)

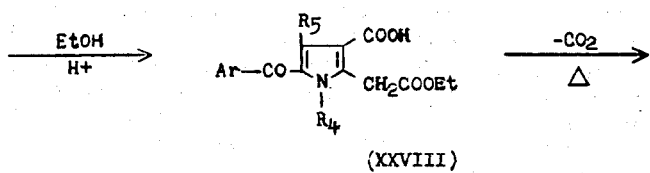

(XXVIII)

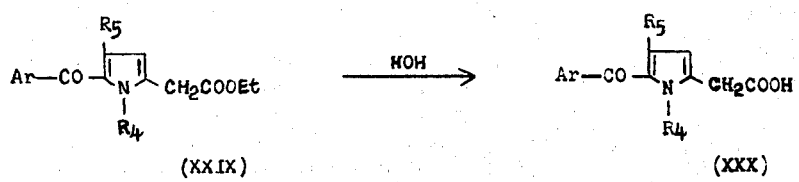

(XXIX)    (XXX)

An alternative procedure for making the compounds of formula (I-c), wherein $R_6$ is hydrogen and $R_4$, $R_5$ and Ar are as previously described except that Ar is other than phenyl substituted with amine, comprises the hydrolysis of the di-ester (XXV), preferably under alkaline conditions, to the corresponding di-acid (XXXI)

(XXXIII) is then acylated with an appropriate aroyl halide, preferably the chloride, of the formula Ar-COCl under Friedel-Crafts reaction conditions to yield the corresponding ester of formula (XXXIV) which in turn may be hydrolyzed to the corresponding acid form (XXXV):

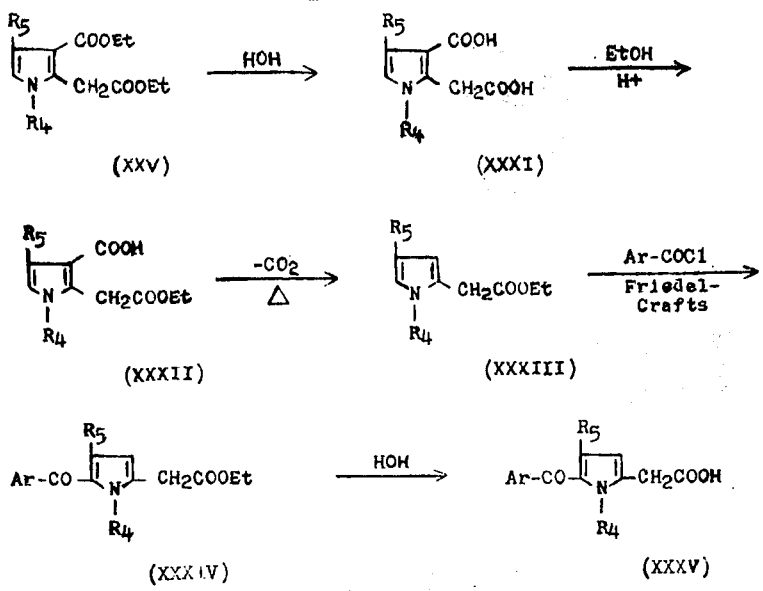

The process of making loweralkyl 1,4-di-loweralkyl-3-loweralkoxycarbonyl-pyrrole-2-acetate (XXV) and the alternative processes for making loweralkyl 1-R4-4-R5-5-aroylpyrrole-2-acetates as exemplified by structures (XXIX) and (XXXIV) are deemed to be novel and, as such, these processes constitute additional features of this invention.

Alkylation of the esters (XXIX) and (XXXIV) according to standard procedures, e.g., with loweralkyl iodide as the alkylating agent in the presence of a strong base such as sodium amide or sodium hydride in a suitable organic solvent such as dimethyl sulfoxide, yields the corresponding α-loweralkyl derivatives of formula (I-e) from which the corresponding α-loweralkyl acids are obtained by conventional hydrolysis. Such acids, together with those of formulas (XXX) and (XXXV) are readily esterified and the amides and substituted amides as defined by "$R_3$" in formula (I-e) are prepared by the methods previously described herein.

The compounds of formula (I-e), wherein Ar is aminosubstituted phenyl, are preferably obtained by reduction of the corresponding 5-nitrobenzoyl esters of formulas (XXIX) and (XXXIV), including the α-loweralkyl derivatives thereof, according to the method previously shown for converting the 5-nitrobenzoyl derivatives of formula (I-a) to the corresponding 5-aminobenzoyl form. Similarly, the thus-obtained lower alkyl 5-aminobenzoyl-1-$R_4$-4-$R_5$-α-$R_6$-pyrrole-2-acetates can be hydrolyzed to the corresponding free acid form from which the desired esters and amides defined by "$R_3$" of formula (I-e) may be obtained according to the usual methods previously described.

The corresponding salts of the acids of formulas (I-a, b, c, d and e) are readily obtained by treating the acids with a slight excess of an equivalent amount of appropriate base, for example, an alkali or alkaline earth metal hydroxide, e.g., sodium hydroxide, potassium hydroxide, barium hydroxide, calcium hydroxide and the like, or with an organic amine base, e.g., a lower alkylamine such as ethylamine, propylamine and the like, or other amines such as benzylamine, piperidine, pyrrolidine and the like.

The subject compounds of formulas (I-a, b, c, d and e) and the therapeutically active salts thereof have useful pharmacological properties which make them suitable for incorporation into conventional pharmaceutical forms for administration. These compounds have been found to possess anti-inflammatory activity as demonstrated in the standard kaolin-induced rat paw edema and cotton pellet granuloma tests at doses generally ranging from 5–100 mg/kg body weight.

In the kaolin-induced rat paw edema assay, the ability of a compound, when administered in a single oral dose, to inhibit the swelling of the rat paw injected with a standard amount (0.1 ml.) of 10% kaolin suspension in saline is measured. For comparative purposes, the activity of the compound to be tested is measured against that produced by the known anti-inflammatory agent, phenylbutazone. Male Holtzman rats are used in the assay. For example, in this test, the compound 5-(p-chlorobenzoyl)-1-methyl-pyrrole-2-acetic acid was found to exhibit an inhibition of about 35% at 12.5 mg/kg; about 47% at 25 mg/kg; and about 45-53% inhibition in doses of 50–100 mg/kg; whereas phenylbutazone exhibited an inhibition of 30–40% at 80 mg/kg and 50–60% at 100 mg/kg.

In the cotton pellet granuloma assay, the ability of a compound, when administered orally to male Holtzman rats daily for seven days, to inhibit the amount of granuloma tissue formed in or around a cotton pellet implanted beneath the skin in the thoracic region of the animal is measured and compared to water controls. The method is described by Charles A. Winter and coworkers in J. Pharmacol., 141, 369 (1963). Analysis of variance is used to determine the significance of the results. For example, in this test, the compound 5-(p-anisoyl)-1-methylpyrrole-2-acetic acid exhibited a granuloma weight of about 71 mg. at a dose of 25 mg/kg as compared to 110 mg. with the water controls; and the compound 5-(p-chlorobenzoyl)-1-methylpyrrole-2-acetonitrile exhibited a granuloma weight of about 98 mg. at a dose of 100 mg/kg as compared to 115 mg. with the water controls.

In the following table, the anti-inflammatory activity of several compounds of formulas (I-a, b, c, d and e) is listed, it being understood tht such compounds are not listed for purposes of limiting the invention thereto, but only to exemplify the useful properties of all the compounds within the scope of formulas (I-a, b, c, d and e), including the pharmaceutically acceptable basic salts thereof.

ample, tablets, capsules, solutions, suspensions, elixirs, injectables and the like.

TABLE I

| KAOLIN-INDUCED PAW EDEMA ASSAY | DOSE (p.o.) mg/kg | % INHIBITION (Average 10 rats) |
|---|---|---|
| 5-(p-chlorobenzoyl)-1-methylpyrrole-2-acetic acid | 25 | 47 |
| 5-(m-chlorobenzoyl)-do | 25 | 41 |
| 5-(o-chlorobenzoyl)-do | 25 | 44 |
| 5-(2',4'-dichlorobenzoyl)-do | 25 | 51 |
| 5-(p-bromobenzoyl)-do | 25 | 42 |
| 5-(p-fluorobenzoyl)-do | 25 | 42 |
| 5-(p-methoxybenzoyl)-do | 25 | 42 |
| 5-(p-methylbenzoyl)-do | 25 | 44 |
| 5-(p-nitrobenzoyl)-do | 100 | 35 |
| 5-(p-aminobenzoyl)-do | 25 | 23 |
| 5-(p-cyanobenzoyl)-do | 100 | 20 |
| 5-benzoyl-do | 25 | 38 |
| 5-(p-chlorobenzoyl)-$\alpha$-methyl-1-methylpyrrole-2-acetic acid | 50 | 56 |
| 5-(p-chlorobenzoyl)-$\alpha$-ethyl-1-methypyrrole-2-acetic acid | 25 | 22 |
| 5-(p-chlorobenzoyl)-pyrrole-2-acetic acid | 25 | 32 |
| 5-(p-chlorobenzoyl)-1-ethylpyrrole-2-acetic acid | 100 | 43 |
| 1-benzyl-5-(p-chlorobenzoyl)-pyrrole-2-acetic acid | 50 | 23 |
| ethyl 5-(p-chlorobenzoyl)-1-methylpyrrole-2-acetate | 25 | 37 |
| methyl 5-(p-chlorobenzoyl)-1-methylpyrrole-2-acetate | 25 | 38 |
| 5-(p-chlorobenzoyl)-1-methylpyrrole-2-acetamide | 50 | 35 |
| 5-(p-chlorobenzoyl)-N-ethyl-1-methylpyrrole-2-acetamide | 25 | 25 |
| 5-(p-chlorobenzoyl)-N,N-diethyl-1-methylpyrrole-2-acetamide | 25 | 36 |
| 5-(p-chlorobenzoyl)-1-methylpyrrole-2-propionic acid | 25 | 63 |
| 5-(p-chlorobenzoyl)-4-methylpyrrole-3-acetic acid | 50 | 43 |
| 5-benzoyl-4-methylpyrrole-2-acetic acid | 100 | 34 |
| (+)-5-(p-chlorobenzoyl)-$\alpha$-methyl-1-methylpyrrole-2-acetic acid | 25 | 62 |
| (−)-5-(p-chlorobenzoyl)-$\alpha$-methyl-1-methylpyrrole-2-acetic acid | 25 | 24 |
| 5-(5-methylthenoyl)-1-methyl-pyrrole-2-acetic acid | 25 | 48 |
| 5-(2-thenoyl)-do | 25 | 63 |
| 5-(p-trifluoromethylbenzoyl)-do | 25 | 60 |
| 5-(o-methylbenzoyl)-do | 12.5 | 34 |
| 5-(p-chlorobenzoyl)-1-methyl-pyrrole-2-acetohydroxamic acid | 25 | 33 |
| 5-(p-chlorobenzoyl)-N-(2-diethyl-aminoethyl)-1-methylpyrrole-2-acetamide | 25 | 27 |

Due to their surprisingly marked potency and/or low toxicity profile, the compounds of formula (I-e) are among the preferred compounds described herein, particularly when $R_2$ is loweralkyl (preferably methyl). For example, in the kaolin-induced rat paw edema assay, a 51% inhibition was observed with 5-(p-chlorobenzoyl)-1,4-dimethylpyrrole-2-acetic acid at a dose of 2.5 mg/kg; 29% inhibition at 3.0 mg/kg and 47% inhibition at 9.0 mg/kg with 5-(p-chlorobenzoyl)-4-ethyl-1-methylpyrrole-2-acetic acid; and 37% inhibition at 3.0 mg/kg and 53% inhibition at 9.0 mg/kg with 5-(p-chlorobenzoyl)-$\alpha$-methyl-1,4-dimethyl-2-acetic acid. Other preferred compounds are those embraced within formulas (I-a, b, c, d and e) wherein the Ar or $Ar_1$ function is halo phenyl, most preferably chlorophenyl, and the $R_2$ or $R_3$ function is COOH or COO-(lower alkyl).

As anti-inflammatory agents, the compounds of formulas (I-a, b, c, d and e) and salts thereof are of value in reducing inflammation and alleviating the symptoms of rheumatic, arthritic and other inflammatory conditions. The compounds can be administered in therapeutic dosages in conventional pharmaceutical formulations for oral and perenteral administration, for ex- As is evident from the previously described methods of forming the subject compounds, many of the compounds of formulas (I-a, b, c, d and e) are also useful as intermediates in the syntheses of other compounds thereunder. For example, the nitriles and esters represented by formulas (IV, V, VI and VII) are useful intermediates in the syntheses of corresponding acids. In addition, the 5-nitrobenzoyl compounds of formulas (I-a) and (I-b) are useful intermediates in the transformation procedure to corresponding 5-aminobenzoyl compounds. Moreover, the acids embraced within formulas (I-a, b, c, d and e) are useful intermediates in the transformation procedures to corresponding esters, amides and basic salts.

Due to the available asymmetric $\alpha$-carbons present in the subject compounds of formulas (I-a) and (I-e), it is evident that their existence in the form of stereochemical isomers (enantiomorphs) is possible. If desired, the resolution and isolation or the production of a particular form can be accomplished by application of general principles known in the art. Said enantiomorphs are naturally intended to be included within the scope of this invention.

The following examples are intended to illustrate, but not to limit, the scope of the present invention.

EXAMPLE I

Ethyl 5-(p-chlorobenzoyl)-1-methylpyrrole-2-acetate

To a solution of 22.0 g. (0.131 mole) of ethyl N-methylpyrrole-2-acetate and 24.5 g. (0.14 mole) of p-chlorobenzoyl chloride in 120 ml. of carbon disulfide is added 35.0 g. (0.262 mole) of anhydrous aluminum chloride over a period of 20 minutes with intermittant cooling to keep the temperature at 25°C. The mixture is stirred for an additional 20 minutes. The carbon disulfide solvent is then decanted and discarded. The red gummy residue is washed with hexane and dilute hydrochloric acid and ice is added to the mixture. The mixture is extracted with ether. The ether solution is shaken with an aqueous solution of dimethylaminopropylamine and washed with dilute hydrochloric acid followed by brine. The solution is dried over magnesium sulfate and treated with charcoal. After removal of the charcoal, the solvent is evaporated in vacuo leaving a partially crystalline red oil as a residue. This material is extracted with three 500 ml. portions of boiling pentane. The combined pentane extracts are evaporated in vacuo and the residue is crystallized from 60 ml. of cold methanol. The resulting solid is collected and washed with cold methanol; there is obtained about 6.3 g. of white crystalline solid, ethyl 5-(p-chlorobenzoyl)-1-methylpyrrole-2-acetate, m.p. 74°–76°C. Recrystallization from methyl cyclohexane raises the melting point to 78°–80°C.

EXAMPLE II 5-(p-Chlorobenzoyl)-1-methylpyrrole-2-acetic acid and its sodium salt: A suspension of 3.06 g. (0.01 mole) of ethyl-5-(p-chlorobenzoyl)-1-methylpyrrole-2-acetate in 25 ml. of 0.5 N sodium hydroxide is refluxed for 30 minutes. About two-thirds of this solution is cooled, washed with ether, and then acidified with dilute hydrochloric acid. The resulting solid precipitate is collected by filtration, dried and recrystallized from ethanol-water to give the product, 5-(p-chlorobenzoyl)-1-metylpyrrole-2-acetic acid; m.p. 189°–191°C. Upon recrystallization from ethanol-water, the melting point is 188°–190°C. The other one-third of the solution is cooled in an ice-bath whereupon the yellow sodium salt of the acid is precipitated and collected by filtration.

Analysis: Calcd. for $C_{14}H_{12}ClNO_3$: C, 60.54; H, 4.36; N, 5.05%. Found: C, 60.54; H, 4.37; N, 5.14%.

EXAMPLE III

By following the procedures of the foregoing examples, except that an equivalent quantity of benzoyl chloride is employed in place of the p-clorobenzoyl-chloride used in Example I, there are obtained as respective products, ethyl 5-benzoyl-1-methyl-pyrrole-2-acetate and 5-benzoyl-1-methyl-pyrrole-2-acetic acid.

EXAMPLE IV

5-Benzoyl-1-methylpyrrole-2-acetonitrile: To a chilled suspension of 9.7 g. (0.07 mole) of alumonum chloride in 45 ml. methylene chloride is added 9 ml. (0.07 mole) benzoyl chloride. The resulting solution is added dropwise to a solution of 1-methylpyrrole-2-acetonitrile in 30 ml. methylene chloride while cooling externally with an ammonium chloride ice bath (temperature below 5°C.). After the addition is complete, the reaction mixture is stirred at 0°C. for fifteen minutes and then poured into ice acidified with 3N hydrochloric acid. The acidic fraction is extracted three times with methylene chloride. The organic fractions are combined and washed consecutively with N,N-dimethyl-1,3-propanediamine and 3N hydrochloric acid. The organic solution is dried over anhydrous magnesium sulfate. The solvent is then evaporated off to yield an oily residue which is column chromatographed on neutral alumina using hexane, benzene and ethylacetate as successive solvents. The first few fractions having ultraviolet absorption in the 240–260 m$\mu$ range contain the desired product. These fractions are combined, the solvent evaporated off and the oily residue, when triturated with methanol, yields the crystalline product, 5-benzoyl-1-methylpyrrole-2-acetonitrile, m.p. 106°–108°C.

EXAMPLE V

5-Benzoyl-1-methylpyrrole-2-acetic acid: A suspension of 2.42 g. (0.11 mole) of 5-benzoyl-1-methylpyrrole-2-acetonitrile, 0.9 g. (0.22 mole) sodium hydroxide, 6 ml. water, and 0.5 ml. ethanol, is stirred and refluxed for one hour. The resulting solution is cooled and extracted in water and chloroform. The aqueous fraction is made acidic with 3N hydrochloric acid. A white solid, 5-benzoyl-1-methylpyrrole-2-acetic acid, precipitates which is filtered and washed with a hexane-ether solution, m.p. 144°–145°C.

Analysis: Calcd. for $C_{14}H_{13}NO_3$: C, 69.12; H, 5.39; N, 5.76%. Found: C, 69.23; H, 5.47; N, 5.78%.

EXAMPLE VI 5-(m-Chlorobenzoyl)-1-methylpyrrole-2-acetonitrile: To a cooled suspension of 16.6 g. (0.12 mole) aluminum chloride in 60 ml. 1,2-dichloroethane is added dropwise 23 g. (0.12 mole) m-chlorobenzoyl-chloride. The resulting suspension is added dropwise to a cooled solution of 15 g. (0.12 mole) 1-methylpyrrole-2-acetonitrile in 60 ml. 1,2-dichloroethane. The reaction mixture is stirred for about twenty minutes at room temperature and then heated and refluxed for three minutes. The reaction is terminated by pouring the mixture into ice acidified with 3N hyrochloric acid. The resulting two fractions are separated. The aqueous fraction is washed with chloroform. The organic fractions are combined and washed consecutively with N,N-dimethyl-1,3-propanediamine, 3N hydrochloric acid and saturated sodium chloride solution. The organic fraction is then dried over anhydrous magnesium sulfate. The solvent is evaporated and the resulting residue is triturated with cold methanol to yield a precipitate of the desired product which is filtered off and set aside. The methanol filtrate is concentrated in vacuo and the remaining oily residue is chromatographed on a column packed with neutral alumina using hexane, benzene and ether as the successive solvents. About 2.5 g. of the desired product are isolated by evaporation of the first few compound-bearing (ether) fractions. The solids are combined and recrystallized from methanol to yield about 3.6 g. of 5-(m-chlorobenzoyl)-1-methylpyrrole-2-acetonitrile, m.p. 122°–127°C.

Analysis: Calcd. for $C_{14}H_{11}ClN_2O$: N, 10.83%. Found: N, 10.52%.

EXAMPLE VII 5-(m-Chlorobenzoyl)-1-methylpyrrole-2-acetic acid: A mixture of 2.8 g. (0.01 mole) of 5-(m-chlorobenzoyl)-1-methylpyrrole-2-acetonitrile, 22 ml. of 1N sodium hydroxide solution and 5 ml. ethanol is stirred at reflux for 15 hours. Some of the ethanol is evaporated. The remaining solution is poured into ice acidified with dilute hydrochloric acid. A white solid, 5-(m-chlorobenzoyl)-1-methylpyrrole-2-acetic acid, precipitates which is recrystallized twice from methanol: water, m.p. 165°C.

Analysis: Calcd. for $C_{14}H_{12}ClNO_3$: C, 60.54; H, 4.36; N, 5.05%. Found: C, 60.61; H, 4.40; N, 4.87%.

EXAMPLE VIII

A. The procedure of Example VI is repeated except that an equivalent quantity of p-bromobenzoyl chloride and p-fluorobenzoyl chloride is used in place of the m-chlorobenzoyl chloride used therein to yield, as respective products:
5-(p-bromobenzoyl)-1-methylpyrrole-2-acetonitrile, m.p. 139°-141°C; and
5-(p-fluorobenzoyl)-1-methylpyrrole-2-acetonitrile, m.p. 134°-136°C.

B. By following the procedure of Example VII, using an equivalent quantity of the foregoing acetonitriles in place of the 5-(m-chlorobenzoyl)-1-methylpyrrole-2-acetonitrile used therein, the following respective acids are obtained:
5-(p-bromobenzoyl)-1-methylpyrrole-2-acetic acid, m.p. 188°C; and
5-(p-fluorobenzoyl)-1-methylpyrrole-2-acetic acid, m.p. 164°-165°C.

EXAMPLE IX 5-(o-Chlorobenzoyl)-1-methylpyrrole-2-acetonitrile: To a cooled suspension of 14 g. (0.105 mole) aluminum chloride in 45 ml. dichloroethane is added dropwise, 18.5 g. (0.105 mole) o-chlorobenzoyl chloride. The resulting solution is added dropwise to a cooled (0°C.) solution of 1-methylpyrrole-2-acetonitrile in 45 ml. dichloroethane keeping the temperature at approximately 10°C. The mixture is stirred at room temperature for about twenty minutes, and then refluxed for three minutes. It is poured into ice acidified with 3N hydrochloric acid and the resulting two layers are separated. The aqueous fraction is extracted twice with chloroform. The organic fractions are combined and washed twice with N,N-dimethyl-1,3-propanediamine, once with 3N hydrochloric acid and once with saturated sodium chloride solution. The organic fraction is dried over anhydrous magnesium sulfate. The solvent is evaporated and the resulting oil is chromatographed on a column packed with neutral alumina using benzene and ether as successive solvents. The first compound-bearing fractions contain the desired product. The solvent is evaporated and the resulting oil crystallizes upon treatment with methanol. The solid product, 5-(o-chlorobenzoyl)-1-methylpyrrole-2-acetonitrile, is purified by recrystallization from benzene:cyclohexane solution, m.p. 80°-85°C.

EXAMPLE X 5-(o-Chlorobenzoyl)-1-methylpyrrole-2-acetic acid: A solution of 2.4 g. (0.009 mole) of 5-(o-chlorobenzoyl)-1-methylpyrrole-2-acetonitrile, 18 ml. of 1N sodium hydroxide and 18 ml. 95% ethanol is stirred and refluxed for seven hours. The ethanol is evaporated off and the remaining solid residue is dissolved in water and washed with chloroform. The aqueous layer is made acidic with 3N hydrochloric acid. An oil precipitates which crystallizes when scratched. The solid is filtered and washed with water and hexane. The solid is purified by recrystallization from methanol:water and again from ether:hexane, m.p. 140°-141°C.

Analysis: Calcd. for $C_{14}H_{12}ClNO_3$: C, 60.54; H, 4.36; N, 5.05%. Found: C, 60.55; H, 4.43; N, 4.91%.

EXAMPLE XI 5-(2',4'-Dichlorobenzoyl)-1-methylpyrrole-2-acetonitrile: To a suspension of 16.6 g. (0.125 mole) of aluminum chloride in 60 ml. 1,2-dichloroethane is added 26.2 g. (0.125 mole) of 2,4-dichlorobenzoyl chloride. The resulting solution is added slowly to a solution of 15 g. (0.125 mole) of 1-methylpyrrole-2-acetonitrile in 60 ml. 1,2-dichloroethane while cooling externally with an ice bath. After the addition is complete, the mixture is stirred for 40 minutes at room temperature followed by heating at reflux for 3 minutes. It is then poured into ice acidified with dilute hydrochloric acid. The organic phase is separated and washed successively with N,N-dimethyl-1,3-propanediamine, 3N hydrochloric acid, and saturated sodium chloride solution. It is then dried over magnesium sulfate and the solvent evaporated. The resulting red oily residue is chromatographed on a column packed with neutral alumina and eluted with benzene and ether. The first compound-bearing fractions upon evaporation yield a white solid, 5-(2',4'-dichlorobenzoyl)-1-methylpyrrole-2-acetonitrile, which is purified by recrystallization from methanol, m.p. 129°-130°C.

Analysis: Calcd. for $C_{14}H_{10}Cl_2N_2O$: N, 9.56%. Found: N, 9.51%.

EXAMPLE XII 5-(2',4'-Dichlorobenzoyl)-1-methylpyrrole-2-acetic acid: A solution of 4.3 g. (0.015 mole) of 5-(2',4'-dichlorobenzoyl)-1-methylpyrrole-2-acetonitrile in 30 ml. 1N sodium hydroxide and 30 ml. 95% ethanol is refluxed overnight. The solution is concentrated and poured into dilute hydrochloric acid. A white solid, 5-(2',4'-dichlorobenzoyl)-1-methylpyrrole-2-acetic acid precipitates which is recrystallized from isopropanol and methanol, m.p. 165°-166°C.

Analysis: Calcd. for $C_{14}H_{11}Cl_2NO_3$: C, 53.86; H, 3.55; N, 4.68%. Found: C, 53.97; H, 3.66; N, 4.69%.

EXAMPLE XIII 5-(p-Toluoyl)-1-methylpyrrole-2-acetonitrile: To a cooled suspension of 26.6 g. (0.2 mole) aluminum chloride in 80 ml. dichloroethane is added dropwise 30.8 g. (0.2 mole) p-toluoyl chloride. The resulting solution is added dropwise to a solution of 1-methylpyrrole-2-acetonitrile in 80 ml. dichloroethane cooled externally with an ice bath. After the addition, the resulitng solution is stirred at room temperature for twenty minutes and then refluxed for three minutes. The solution is poured into ice acidified with dilute hydrochloric acid. The organic and aqueous fractions are separated. The aqueous fraction is extracted once with chloroform. The organic fractions are combined and washed successively with N,N-dimethyl-1,3-propanediamine, dilute hydrochloric acid, saturated sodium bicarbonate solution and saturated sodium chloride solution. The organic fraction is dried over anhydrous magnesium sulfate. The solvent is then evaporated off. Upon trituration of the residue with methanol, a solid crystallizes, 5-p-toluoyl)-1-methylpyrrole-2-acetonitrile, which is removed by filtration and purified by recrystallization from benzene. Additional product is isolated from the mother liquors which are combined, concentrated in vacuo and the resulting oily residue column chromatographed on neutral alumina using hexane, benzene and ether as successive solvents. The product is isolated by concentrating in vacuo the first few major compound-bearing fractions (10% ether in benzene). The solids are combined and recrystallized from methanol and then from benzenehexane, m.p. 102°–105°C.

EXAMPLE XIV 5-(p-Toluoyl)-1-methylpyrrole-2-acetic acid: A solution of 3.67 g. (0.015 mole) of 5-(p-toluoyl)-1-methylpyrrole-2-acetonitrile, 24 ml. of 1N sodium hydroxide, and 50 ml. of 95% ethanol is stirred and refluxed for twenty-four hours. The resulting solution is poured into ice acidified with dilute hydrochloride acid. A white solid precipitates which is extracted into ether. The ether phase is washed with a saturated solution of sodium chloride and dried over anhydrous magnesium sulfate. The solvent is evaporated and a white solid, 5-(p-toluoyl)-1-methylpyrrole-2-acetic acid, is obtained which is recrystallized twice from isopropanol, m.p. 155°–157°C.

EXAMPLE XV

A. By repeating the procedure of Example XI, except that an equivalent quantity of o-toluoyl chloride, m-toluoyl chloride, p-ethylbenzoyl chloride and 3,4-dmethylbenzoyl chloride is used in lieu of the 2,4-dichlorobenzoyl chloride used therein, there are obtained as respective products the corresponding 5-(o-toluoyl), 5-(m-toluoyl), 5-(p-ethylbenzoyl) and 5-(3′,-4′-dimethylbenzoyl) derivatives of 1-methylpyrrole-2-acetonitrile.

B. The procedure of Example XII is repeated, using an equivalent quantity of each of the foregoing acetonitriles in place of the 5-(2′,4′-dichlorobenzoyl)-1-methylpyrrole-2-acetonitrile used therein, to yield as respective products the corresponding 5-(o-toluoyl), 5-(m-toluoyl), 5-(p-ethylbenzoyl) and 5-(3′,4′-dimethylbenzoyl) derivatives of 1-methylpyrrole-2-acetic acid.

EXAMPLE XVI

Methyl 5-(p-anisoyl)-1-methylpyrrole-2-acetate: A solution of 17.0 g. (0.1 mole) of p-anisoyl chloride and 13.3 g. (0.1 mole) of aluminum chloride in 200 ml. of methylene chloride is added over 5 minutes to a solution of methyl 1-methylpyrrole-2-acetate in 100 ml. of methylene chloride at ice bath temperature. The mixture is stirred for 25 minutes and poured into ice acidified with dilute hydrochloric acid. The organic layer is separated and the aqueous layer is washed with methylene chloride. The combined organic solutions are washed successively with dimethylaminopropylamine solution, dilute hydrochloric acid and brine and then dried over anhydrous magnesium sulfate. The solvent is evaporated in vacuo to give a dark oily residue which is crystallized from 40 ml. of cold methanol. The solid is collected by filtration, washed with cold methanol and recrystallized from methanol to give white crystalline methyl 5-(p-anisoyl)-1-methylpyrrole-2-acetate, m.p. 104°–105°C.

EXAMPLE XVII 5-(p-Anisoyl)-1-methylpyrrole-2-acetic acid: A solution of 3.00 g. (0.0105 mole) of methyl 5-(p-anisoyl)-1-methylpyrrole-2-acetate in 12 ml. (0.012 mole) of 1N sodium hydroxide solution and 5 ml. of 95% ethanol is refluxed for 30 minutes. The solution is diluted with water and the ethanol is evaporated in vacuo. The solution is filtered and the filtrate acidified with dilute hydrochloric acid. The precipitated solid is collected by filtration, dried and recrystallized from methanol-water to give about 2.4 g. (87% yield) of white 5-(p-anisoyl)-1-methylpyrrole-2-acetic acid, m.p. 170°–171°C.

Analysis: Calcd. for $C_{15}H_{15}NO_4$: C, 65.92; H, 5.53; N, 5.13%. Found: C, 66.01; H, 5.62; N, 5.12%.

EXAMPLE XVIII

By repeating the procedures of Examples XVI and XVII successively, except that an equivalent quantity each of m-anisoyl chloride and p-ethoxybenzoyl chloride is initially employed in place of p-anisoyl chloride, there are obtained as ester products, the corresponding 5-(m-anisoyl) and 5-(p-ethoxybenzoyl) derivatives of methyl 1-methylpyrrole-2-acetate, and as acid products, the corresponding 5-(m-anisoyl) and 5-(p-ethoxybenzoyl) derivatives of 1-methylpyrrole-2-acetic acid, respectively.

EXAMPLE XIX 5-(3′Chloro-p-toluoyl)-1-methylpyrrole-2-acetonitrile: 21.4 Grams (0.114 mole) of 3-chloro-4-methylbenzoylchloride is added to a suspension of 15.2 g. (0.114 mole) aluminum chloride in 50 ml. 1,2-dichloroethane. The resulting solution is added dropwise to a chilled solution of 13.7 g. (0.114 mole) of 1-methylpyrrole-2-acetonitrile in 50 ml. 1,2-dichloroethane. After the addition is complete, the mixture is stirred for ten minutes at room temperature and then heated to reflux for three minutes. It is poured into ice acidified with dilute HCl. The organic phase is separated and washed consecutively with N,N-dimethyl-1,3-propanediamine, 3N hydrochloric acid and saturated sodium chloride solution. It is then dried over anhydrous magnesium sulfate and the solvent evaporated off. A white solid, 5-(3′-chloro-p-toluoyl)-1-methylpyrrole-2-acetonitrile, precipitates from the resulting oily residue upon trituration with methanol which is purified by recrystallization from methanol, m.p. 116°–118°C.

Analysis: Calcd. for $C_{15}H_{13}ClN_2O$: N, 10.26%. Found: N, 10.38%.

EXAMPLE XX 5-(3′-Chloro-p-toluoyl)-1-methylpyrrole-2-acetic acid: A solution of 3.5 g. (0.0013 mole) of 5-(3′-chloro-p-toluoyl)-1-methylpyrrole-2-acetonitrile in 18 ml. 95% ethanol and 26 ml. 1N sodium hydroxide is heated at reflux overnight. The reaction mixture is then cooled and poured into dilute hydrocloric acid. The resulting white precipitate, 5-(3′-chloro-p-toluoyl)-1-methylpyrrole-2-acetic acid, is filtered off and purified by recrystallization once from isopropanol, m.p. 176°–178°C.

EXAMPLE XXI

By repeating the Friedel-Crafts procedures of Example XVI with an equivalent amount of an appropriately substituted benzoyl chloride, the following 5-aroyl derivatives of methyl 1-methylpyrrole-2-acetate are obtained:

methyl 5-(3',4'-dimethoxybenzoyl)-1-methylpyrrole-2-acetate;
methyl 5-(3',5'-dinitrobenzoyl)-1-methylpyrrole-2-acetate;
methyl 5-(3'-bromo-4'-chlorobenzoyl)-1-methylpyrrole-2-acetate;
methyl 5-(2',3',5'-tribromobenzoyl)-1-methylpyrrole-2-acetate; and
methyl 5-(3',4',5'-trimethoxybenzoyl)-1-methylpyrrole-2-acetate.

EXAMPLE XXII

The transformation of an acetic acid ester function to an acetic acid function according to the hydrolysis procedure of Example XVII is repeated with an equivalent amount of each of the pyrrole-acetates obtained in Example XXI to yield, as respective products, the corresponding 5-aroyl-1-methylpyrrole-2-acetic acids.

EXAMPLE XXIII 5-(p-Nitrobenzoyl)-1-methylpyrrole-2-acetonitrile:
A solution of 46.4 g. (0.25 mole) of p-nitrobenzoyl chloride in 100 ml. 1,2-dichloroethane is added portionwise to a suspension of 32.2 g. (0.25 mole) aluminum cloride in 100 ml. 1,2-dichloroethane. This mixture is added dropwise to a chilled solution of 30.0 g. (0.25 mole) 1-methylpyrrole-2-acetonitrile in 100 ml. 1,2-dichloroethane. After the addition is complete, the mixture is stirred for twenty minutes at room temperature and then refluxed for four minutes. It is poured into ice acidified with 2N hydrochloric acid. The organic phase is separated and washed successively with N,N-dimethyl-1,3-propanediamine, 3N hydrochloric acid and saturated sodium chloride solution. It is then dried over magnesium sulfate and the solvent evaporated in vacuo. The resulting semi-solid residue is triturated with cold methanol from which the product, 5-(p-nitrobenzoyl)-1-methylpyrrole-2-acetonitrile, crystallizes. It is removed by filtration and purified by recrystallization from acetone, m.p. 167°–169°C.

EXAMPLE XXIV 5-(p-Aminobenzoyl)-1-methylpyrrole-2-acetonitrile:
A solution of 7 g. (0.026 mole) of 5-(p-nitrobenzoyl)-1-methylpyrrole-2-acetonitrile in 450 ml. of ethyl acetate containing 1 g. palladium-on-carbon catalyst is hydrogenated in a Parr shaker under 44 p.s.i. of hydrogen until the theoretical amount of hydrogen is consumed. The catalyst is filtered off and the solvent evaporated in vacuo. About 6.0 g. (97% yield) of a yellow solid, 5-(p-aminobenzoyl)-1-methylpyrrole-2-acetonitrile remains, m.p. 137°–142°C.

EXAMPLE XXV 5-(p-Aminobenzoyl)-1-methylpyrrole-2-acetic acid:
A suspension of 6.0 g. (0.025 mole) of 5-(p-aminobenzoyl)-1-methylpyrrole-2-acetonitrile, 25 ml. 95% ethanol and 25 ml. /N sodium hydroxide is refluxed overnight. The ethanol is then evaporated in vacuo and the remaining suspensions is poured into ice acidified with dilute hydrochloric acid to pH 5. The resulting solid is partitioned between sodium bicarbonate solution and chloroform. The insoluble substances are filtered from the two-phase mixture. The sodium bicarbonate layer is separated and acidified slowly with dilute hydrochloric acid. Solids precipitate at various pHs which are separated by filtration. The desired product, 5-(p-aminobenzoyl)-1-methylpyrrole-2-acetic acid, precipitates at pH 3, m.p. 173°–175°C.

EXAMPLE XXVI

Ethyl 5-(p-Nitrobenzoyl)-1-methylpyrrole-2-acetate:
A solution of 5.5 g. (0.03 mole) of p-nitrobenzoyl chloride in 60 ml. methylene chloride is added to a suspension of 3.9 g. (0.03 mole) aluminum chloride in 20 ml. methylene chloride. The resulting suspension is added dropwise to a chilled (−15°C.) solution of ethyl 1-methylpyrrole-2-acetate in 50 ml. methylene chloride. The solution is stirred for 15 minutes at −10°C. and at room temperature for 15 minutes. The reaction mixture is poured into ice-dilute hydrochloric acid. The organic phase is separated and washed successively with N,N-dimethyl-1,3-propanediamine, 3N hydrochloric acid and a saturated solution of sodium chloride, dried over anhydrous magnesium sulfate, and the solvent evaporated in vacuo. A solid, ethyl 5-(p-nitrobenzoyl)-1-methylpyrrole-2-acetate, crystallizes from the remaining oily residue which is isolated by recrystallization from methanol, m.p. 103°–106°C.

EXAMPLE XXVII 5-(p-Nitrobenzoyl)-1-methylpyrrole-2-acetic acid: A solution of 3.2 g. (0.01 mole) of ethyl 5-(p-nitrobenzoyl)-1-methylpyrrole-2-acetate and 25 ml. ethanol is brought to reflux. To this is added dropwise 10 ml. of 1N sodium hydroxide solution. After the addition is complete, the ethanol is evaporated and the residue is acidified with dilute hydrochloric acid. The resulting solid, 5-(p-nitrobenzoyl)-1-methylpyrrole-2-acetic acid, is separated by filtration and purified by recrystallization from ethanol, m.p. 192°–195°C.

EXAMPLE XXVIII

Ethyl 5-(p-cyanobenzoyl)-1-methylpyrrole-2-acetate:
A solution of 5.0 g. (0.03 mole) of p-cyanobenzoyl chloride in 60 ml. of methylene chloride is added to a suspension of 40 g. of aluminum chloride in 30 ml. methylene chloride. The resulting mixture is added dropwise to a chilled solution of 5.0 g. (0.03 mole) of ethyl 1-methylpyrrole-2-acetate in 15 ml. of methylene chloride. The resulting mixture is stirred at room temperature for 20 minutes, and then poured into ice acidified with dilute hydrochloric acid. The organic phase is separated, washed successively with N,N-dimethylaminopropylamine, 3N hydrochloric acid and brine, and dried over anhydrous magnesium sulfate. The solvent is evaporated in vacuo. The resulting solid, which separates from the oily residue on standing, is recrystallized from methanol to give pure ethyl 5-(p-cyanobenzoyl)-1-methylpyrrole-2-acetate, m.p. 117°–120°C.

EXAMPLE XXIX 5-(p-cyanobenzoyl)-1-methylpyrrole-2-acetic acid: A solution of 0.5 g. (0.0017 mole) of ethyl 5-(p-cyanobenzoyl)-1-methylpyrrole-2-acetate in 3 ml. ethanol is brought to reflux and 1.7 ml. of 1N sodium hydroxide solution is added dropwise. The mixture is refluxed for 3 minutes and the ethanol is then evaporated in vacuo. The residue is diluted with water and acidified with dilute hydrochloric acid. A white solid precipitates, 5-(p-cyanobenzoyl)-1-methylpyrrole-2-acetic acid, which is collected by filtration and dried, m.p. 196°–198°C.

EXAMPLE XXX

Methyl 5-(p-methylthiobenzoyl)-1-methylpyrrole-2-acetate is obtained by repeating the procedure of Example XVI except that an equivalent quantity of p-methylthiobenzoyl chloride is used in place of the p-anisoyl chloride used therein.

EXAMPLE XXXI 5-(p-Methylthiobenzoyl)-1-methylpyrrole-2-acetic acid is obtained by repeating the hydrolysis procedure of Example XVII except that the hydrolysis is performed on an equivalent amount of the ester obtained from Example XXX.

EXAMPLE XXXII

Ethyl 5-(p-chlorobenzoyl)-$\alpha$-methyl-1-methylpyrrole-2-acetate: A solution of 6.68 g. (0.0219 mole) of ethyl 5-(p-chlorobenzoyl)-1-methylpyrrole-2-acetate in 50 ml. of ether is added to a solution of 0.94 g. (0.024 mole) of sodamide in about 150 ml. of liquid ammonia at −33°C. The mixture is allowed to reflux for 15 minutes and 3.10 g. (0.0219 mole) of methyl iodide is added. The mixture is stirred for one hour; then the ammonia is allowed to boil off. Ether and enough ammonium chloride to neutralize any anion are added. The mixture is poured into dilute hydrochloric acid and the ether solution is separated and washed with sodium bisulfite solution, sodium bicarbonate solution and brine. It is dried over anhydrous magnesium sulfate and evaporated to give about 6.8 g. of an oily residue whch crystallizes upon standing. The solid is recrystallized successively from cyclohexane and methanol to give a white crystalline solid, ethyl 5-(p-chlorobenzoyl)-$\alpha$-methyl-1-methylpyrrole-2-acetate, m.p. 67°–68°C.

EXAMPLE XXXIII

A. 5-(p-Chlorobenzyl)-$\alpha$-methyl-1-methylpyrrole-2-acetic acid: A solution of 4.05 g. (0.0126 mole) of ethyl 5-(p-chlorobenzoyl)-$\alpha$-methyl-1-methylpyrrole-2-acetate, 15 ml. of 1N sodium hydroxide solution and 2 ml. of ethanol is refluxed for 30 minutes. The solution is cooled, diluted with water and filtered. The filtrate is acidified with dilute hydrochloric acid. The precipitated solid is collected and recrystallized from methanol-water to give a white crystalline solid, 5-(p-chlorobenzoyl)-$\alpha$-methyl-1-methylpyrrole-2-acetic acid, m.p. 135°–136°C.

Analysis: Calcd. for $C_{15}H_{14}ClNO_3$: C, 61.76; H, 4.83; N, 4.82% Found : C, 61.68: H, 4.86; N, 4.89%

B. The $\alpha$-methyl acid of Example XXXIII-A is heated under reflux for a few hours with an excess of anhydrous methanol in the presence of a trace of dry hydrogen chloride to yield the corresponding methyl ester.

EXAMPLE XXXIV 5-(p-Chlorobenzoyl)-$\alpha$-methyl-1-methylpyrrole-2-acetonitrile: To a suspension of sodium hydride (12.2 g. of 50% w/w NaH in mineral oil) in 1,2-dimethoxyethane is added 5-(p-chlorobenzoyl)-1-methylpyrrole-2-acetonitrile (62.6 g., 0.24 mole) in 1,2-dimethoxyethane over a period of ½ hr. at room temperature. After the addition is complete, the mixture is stirred for 1 hour and then 35 g. (0.25 mole) of methyl iodide is added. The reaction mixture is stirred for an additional 3 hrs., concentrated under reduced pressure, diluted with water and extracted with chloroform. After drying, the chloroform is removed leaving a brown solid residue which is triturated with cold methanol to give yellow crystals of 5-(p-chlorobenzoyl)-$\alpha$-methyl-1-methylpyrrole-2-acetonitrile, m.p. 145°–148°C. Two recrystallizations from methanol raises the m.p. to 151.5°–152.5°C.

EXAMPLE XXXV 5-(p-Chlorobenzoyl)-$\alpha$-methyl-1-methylpyrrole-2-acetic acid: A 27.1 g. (0.1 mole) sample of 5-(p-chlorobenzoyl)-$\alpha$-methyl-1-methylpyrrole-2-acetonitrile is hydrolyzed by refluxing for 16 hours with 8 g. (0.2 mole) of sodium hydroxide in 350 ml. of aqueous ethanol. Upon concentration in vacuo, the sodium salt separates which is filtered off and dissolved in water. After acidification with dilute HCl, the corresponding acid, 5-(p-chlorobenzoyl)-$\alpha$-methyl-1-methylpyrrole-2-acetic acid, precipitates. The original basic filtrates are also acidified, extracted with chloroform and concentrated. The residual solid is combined with the previous solid and recrystallized from methanol-water to give the pure product, 5-(p-chlorobenzoyl)-$\alpha$-methyl-1-methylpyrrole-2-acetic acid, m.p. 139°–141°C.

EXAMPLE XXXVI 5-(p-Chlorobenzoyl)-$\alpha$-ethyl-1-methylpyrrole-2-acetic acid: A solution of 6.5 g (0.021 mole) of ethyl 5-(p-chlorobenzoyl)-1-methylpyrrole-2-acetate in 60 ml. of ether is added to a suspension of 1.25 g. (0.032 mole) of sodamide in 150 ml. of refluxing liquid ammonia. After 10 minutes, 4.98 g. (0.032 mole) of ethyl iodide is added. The mixture is stirred for 1.5 hrs. and an additional 1.0 g. (0.0064 mole) of ethyl iodide is added. Stirring is continued for 30 minutes and ammonium chloride is then added to neutralize any anion. The mixture is allowed to warm to room temperature and the ammonia allowed to escape. Ether is added and the mixture poured into dilute hydrochloric acid. The ether layer is separated and the aqueous layer is washed with ether. The combined ether solutions are washed successively with sodium bisulfite solution and brine and then dried over anhydrous magnesium sulfate. The solvent is evaporated in vacuo to give about 7.4 g. of a yellow oily residue containing ethyl 5-(p-chlorobenzoyl)-$\alpha$-ethyl-1-methylpyrrole-2-acetate, which is used as such in the following transformation to acid procedure.

A 6.9 g. sample of the oily residue is dissolved in 30 ml. of ethanol and 11.4 ml. of 1N sodium hydroxide is added. The mixture is refluxed for 1 hr. The solvent is then evaporated in vacuo and the residue partitioned between ether and water. The aqueous layer is separated and acidified with dilute hydrochloric acid. The precipitated oil, which is separated, crystallizes on scratching to give a solid, 5-(p-chlorobenzoyl)-$\alpha$-ethyl-1-methylpyrrole-2-acetic acid, which is collected and dried, m.p. 108°–112°C. After successive recrystallizations from ether-methylcyclohexane, benzene-hexane, methylcyclohexane and ether-hexane, the m.p. is 110°–114°C.

Analysis: Calcd. for $C_{16}H_{16}ClNO_3$: C, 62.84; H, 5.27; N, 4.58% Found : C, 63.01; H, 5.36; N, 4.61%

EXAMPLE XXXVII

The alkylation and ester-to-acid transformation procedures of Example XXXXVI are repeated except that an equivalent amount of an appropriate 5-aroyl-1-methylpyrrole-2-acetic acid alkyl ester and an equivalent amount of an appropriate alkyl halide alkylating agent are employed to yield the following products:
5-benzoyl-α-(n-butyl)-1-methylpyrrole-2-acetic acid;
5-(p-methoxybenzoyl)-α-methyl-1-methylpyrrole-2-acetic acid;
5-benzoyl-α-(n-propyl)-1-methylpyrrole-2-acetic acid; and
5-(p-cyanobenzoyl)-α-methyl-1-methylpyrrole-2-acetic acid.

EXAMPLE XXXVIII

The alkylation and nitrile-to-acid transformation procedures of Examples XXXIV and XXXV, respectively, are repeated except that an equivalent amount of an appropriate 5-aroyl-1-methylpyrrole-2-acetonitrile and an equivalent amount of an appropriate alkyl halide alkylating agent are employed to yield the following products:
5-(m-chlorobenzoyl)-α-methyl-1-methylpyrrole-2-acetic acid;
5-(p-fluorobenzoyl)-α-ethyl-1-methylpyrrole-2-acetic acid;
5-(p-methylbenzoyl)-α-ethyl-1-methylpyrrole-2-acetic acid;
5-(2',4'-dichlorobenzoyl)-α-methyl--methylpyrrole-2-acetic acid; and
5-(3'-chloro-4'-methylbenzoyl)-α-ethyl-1-methylpyrrole-2-acetic acid.

EXAMPLE XXXXIX 5-(p-Chlorobenzoyl)-pyrrole-2-acetonitrile: To a chilled suspension of 26.80 g. (0.2 mole) of aluminum chloride in 110 ml. of methylene chloride is added dropwise 35 g. (0.2 mole) of p-chlorobenzoyl chloride. The mixture is added dropwise to a solution of 21.22 g. (0.2 mole) of pyrrole-2-acetonitrile in 125 ml. methylene chloride which is cooled externally with an ammonium chloride ice bath. After addition is complete, the reaction mixture is stirred for ten minutes at 0°C. and then poured into ice acidified with dilute hydrochloric acid. A solid precipitate, 5-(p-chlorobenzoyl)-pyrrole-2-acetonitrile, which is filtered off, washed with hot methanol and dried, m.p. 203°–205°C.

EXAMPLE XL 5-(p-Chlorobenzoyl)-pyrrole-2-acetic acid: A solution of 3.6 g. (0.015 mole) of 5-(p-chlorobenzoyl)-pyrrole-2-acetonitrile, 30 ml. 1N sodium hydroxide solution, and 30 ml. 95% ethanol is refluxed and stirred for 6 hours. The ethanol is evaporated off in vacuo. The resulting solid is dissolved in water and the solution filtered from insolubles. The filtrate is acidified with dilute hydrochloric acid. A white solid precipitates, 5-(p-chlorobenzoyl)-pyrrole-2-acetic acid, which is purified by recrystallization from acetone:water (1:1), m.p. 210°C.

EXAMPLE XLI

The procedure of Example XXXIX is followed to prepare 5-aroyl-1-$R_1$-pyrrole-2-acetonitriles wherein $R_1$ is hydrogen, For example, by repeating such procedure, except that an equivalent amount of an appropriate benzoyl chloride is used in place of the p-chlorobenzoyl chloride used therein, the following pyrrole-acetonitriles are obtained as respective products:
5-benzoyl-pyrrole-2-acetonitrile;
5-(p-fluorobenzoyl)-pyrrole-2-acetonitrile;
5-(p-methylbenzoyl)-pyrrole-2-acetonitrile;
5-(p-methoxybenzoyl)-pyrrole-2-acetonitrile;
5-(3'-chloro-4'-methoxybenzoyl)-pyrrole-2-acetonitrile; and
5-(2',4'-dichlorobenzoyl)-pyrrole-2-acetonitrile.

EXAMPLE XLII

The precedure of Example XL is repeated using an equivalent amount of each pyrrole-acetonitrile obtained in Example XLI in place of 5-(p-chlorobenzoyl)-pyrrole-2-acetonitrile to yield, as respective products:
5-benzoyl-pyrrole-2-acetic acid;
5-(p-fluorobenzoyl)-pyrrole-2-acetic acid;
5-(p-methylbenzoyl)-pyrrole-2-acetic acid;
5-(p-methoxybenzoyl)-pyrrole-2-acetic acid;
5-(3'-chloro-4'-methylbenzoyl)-pyrrole-2-acetic acid; and
5-(2',4'-dichlorobenzoyl)-pyrrole-2-acetic acid.

EXAMPLE XLIII 5-(p-Chlorobenzoyl)-1-ethylpyrrole-2-acetonitrile:
A mixture of 24.4 g. (0.1 mole) 5-(p-chlorobenzyl)-pyrrole-2-acetonitrile, 41.7 g. (0.3 mole) of potassium carbonate and 16.1 g. (0.105 mole) of ethyl iodide in 300 ml. of methylethylketone is refluxed overnight. The reaction mixture is then poured into water and extracted with chloroform. The organic solutions are combined, dried over anhydrous magnesium sulfate and the solvent evaporated in vacuo. The residue is crystallized from 2-propanol to give about 13 g. of crude solid. The solid is sublimed overnight at 140°C. and 0.025 mm. Hg. The sublimate is successively recrystallized from 2-propanol, benzene and hexane to give 5-(p-chlorobenzoyl)-1-ethylpyrrole-2-acetonitrile as a white solid, m.p. 145°–147°C.

Analysis: Calcd. for $C_{15}H_{13}ClN_2O$: N, 10.2%. Found: N, 10.54%.

EXAMPLE XLIV 5-(p-Chlorobenzoyl)-1-ethylpyrrole-2-acetic acid: A suspension of 3.52 g. (0.013 mole) of 5-(p-chlorobenzoyl)-1-ethylpyrrole-2-acetonitrile in 26 ml. 1N sodium hydroxide and 50 ml. of ethanol is refluxed for six hours. The mixture is then diluted with water and cooled. A solid precipitates which is filtered off and set aside. The ethanol is evaporated from the filtrate in vacuo. The collected precipitate is added to the concentrated filtrate and the mixture is extracted with chloroform. The aqueous phase is separated, acidified with dilute hydrochloric acid, and the resulting precipitate (A) is collected by filtration and dried. The chloroform phase is evaporated and the residue refluxed with 12 ml. of 1N sodium hydroxide and 24 ml. of ethanol for 6 hours. The ethanol is evaporated in vacuo and the remaining solution is diluted with water and washed with chloroform. The aqueous solution is acidified with dilute hydrochloric acid and the precipitated solid (B) is collected and dried. The two samples of acidic material (A and B) are combined and recrystallized from aqueous isopropanol to give 5-(p-chlorobenzoyl)-1-ethylpyrrole-2-acetic acid as a white solid, m.p. 149°–153°C.

Analysis: Calcd. for $C_{15}H_{14}ClNO_3$: C, 61.75; H, 4.83; N, 4.80%. Found: C, 61.78; H, 4.94; N, 4.96%.

EXAMPLE XLV

The N-alkylation procedure of Example XLIII is followed to prepare 5-aroyl-1-$R_1$-pyrrole-2-acetonitriles wherein $R_1$ is lower alkyl. For example, by repeating such procedure with an equivalent amount of an appropriate N-unsubstituted 5-aroyl-pyrrole-2-acetonitrile and an equivalent amount of an appropriate alkyl halide as the N-alkylating agent, the following respective products are obtained:
5-benzoyl-1-ethylpyrrole-2-acetonitrile;
5-(p-methylbenzoyl)-1-(n-propyl)pyrrole-2-acetonitrile;
5-(p-methoxybenzoyl)-1-ethylpyrrole-2-acetonitrile; and
5-(2',4'-dichlorobenzoyl)-1-(n-butyl)pyrrole-2-acetonitrile.

EXAMPLE XLVI

The nitrile-to-acid transformation procedure of Example XLIV is repeated, except that an equivalent amount of each acetonitrile obtained in Example XLV is used as the starting acetonitrile to yield the following respective products:
5-benzoyl-1-ethylpyrrole-2-acetic acid;
5-(p-methylbenzoyl)-1-(n-propyl)pyrrole-2-acetic acid;
5-(p-methoxybenzoyl)-1-ethylpyrrole-2-acetic acid; and
5-(2',4'-dichlorobenzoyl)-1-(n-butyl)pyrrole-2-acetic acid.

EXAMPLE XLVII

The alkylation and transformation procedures of Examples XXXIV and XXXV, respectively, are repeated, except that an equivalent amount of each alkyl-pyrrole-acetonitrile obtained in Examples XLIII and XLV is used in place of the starting acetonitrile used in Example XXXIV, and an equivalent amount of an appropriate alkyl halide is used as the alkylating agent, to yield the following respective products:
5-(p-chlorobenzoyl)-α-methyl-1-ethylpyrrole-2-acetic acid;
5-benzoyl-α-methyl-1-ethylpyrrole-2-acetic acid;
5-(p-methylbenzoyl)-α-ethyl-1-(n-propyl)pyrrole-2-acetic acid; and
5-(2',4'-dichlorobenzoyl)-α-methyl-1-(n-butylpyrrole)-2-acetic acid.

EXAMPLE XLVIII

1-Benzyl-5-(p-chlorobenzoyl)-pyrrole-2-acetonitrile: A solution of 8.43 ml. (0.0663 mole) of p-chlorobenzoyl chloride and 8.8 g. (0.0663 mole) of aluminum chloride in 100 ml. of 1,2-dichloroethane is added to a solution of 13.0 g. (0.0663 mole) of 1-benzylpyrrole-2-acetonitrile in 50 ml. of 1,2-dichloroethane at 5°C. over a 5 minute period. The mixture is stirred for 15 minutes and then heated quickly to reflux for 3 minutes. The reaction mixture is poured into ice-hydrochloric acid and then filtered. The aqueous layer is separated and washed with chloroform. The combined organic solutions are washed successively with N,N-dimethylaminopropylamine solution, dilute hydrochloric acid, and brine and then dried over anhydrous magnesium sulfate. The solvent is evaporated and the oily residue dissolved in benzene-methylcyclohexane and seeded with crystals of 1-benzyl-4-(p-chlorobenzoyl)-pyrrole-2-acetonitrile. After crystallization of the latter substance is complete, the mother liquor is filtered and evaporated and the residue crystallized from methanol. The crystals thus obtained are recrystallized from methanol to give 1-benzyl-5-(p-chlorobenzoyl)-pyrrole-2-acetonitrile as a yellow solid, m.p. 104°–106°C.

EXAMPLE XLIX

1-Benzyl-5-(p-chlorobenzoyl)-pyrrole-2-acetic acid: A suspension of 3.0 g. (0.009 mole) of 1-benzyl-5-(p-chlorobenzoyl)-pyrrole-2-acetonitrile in 20 ml. of ethanol and 18 ml. (0.018 mole) of 1N sodium hydroxide is refluxed for 6 hours. The mixture is diluted with water and the ethanol evaporated in vacuo. The solution is washed with chloroform and ether and acidified with 3N hydrochloric acid. The precipitated solid is collected and dried in vacuo to give about 2.8 g. (91% yield) of 1-benzyl-5-(p-chlorobenzoyl)-pyrrole-2-acetic acid as white crystals, M.P. 162°–163°C.

Analysis: Calcd. for $C_{20}H_{15}ClNO_3$: C, 67.70; H, 4.65; N, 3.96%. Found: C, 67.79; H, 4.65; N, 3.97%.

EXAMPLE L

The procedure of Example XLVIII is followed to prepare 5-aroyl-1-$R_1$-pyrrole-2-acetonitriles wherein $R_1$ is benzyl. For example, by repeating such procedure with an equivalent amount of an appropriate benzoyl chloride in place of the p-chlorobenzoyl chloride used therein, the following respective products are obtained:
1-benzyl-5-benzoyl-pyrrole-2-acetonitrile;
1-benzyl-5-(p-bromobenzoyl)-pyrrole-2-acetonitrile;
1-benzyl-5-(p-ethoxybenzoyl)-pyrrole-2-acetonitrile;
1-benzyl-5-(2',4'-dichlorobenzoyl)-pyrrole-2-acetonitrile; and
1-benzyl-5-(3',4'-dimethylbenzoyl)-pyrrole-2-acetonitrile.

EXAMPLE LI

A. The nitrile-to-acid transformation procedure of Example XLIX is followed using an equivalent amount of each acetonitrile obtained in Example L to yield, as respective products, the corresponding 1-benzyl-5-aroyl-pyrrole-2-acetic acids.

B. Each of the 1-benzyl acids obtained from Examples XLIX and LI-A is heated under reflux for a few hours with an excess of anhydrous methanol in the presence of a trace of dry hydrogen chloride to yield the corresponding methyl esters.

EXAMPLE LII

The alkylation and transformation procedures of Examples XXXIV and XXXV, respectively, are repeated, except that an equivalent amount of an appropriate 1-benzyl-5-aroyl-pyrrole-2-acetonitrile and an equivalent amount of an appropriate alkyl halide as the alkylating agent are used to yield the following respective products:
1-benzyl-5-(p-chlorobenzoyl)-α-methyl-pyrrole-2-acetic acid;
1-benzyl-5-benzoyl-α-(n-propyl)-pyrrole-2-acetic acid;
1-benzyl-5-(p-bromobenzoyl)-α-ethyl-pyrrole-2-acetic acid;
1-benzyl-5-(p-ethoxybenzoyl)-α-methyl-pyrrole-2-acetic acid;
1-benzyl-5-(2',4'-dichlorobenzoyl)-α-ethyl-pyrrole-2-acetic acid; and 1-benzyl-5-(3',4'-dimethylbenzoyl)-α-methyl-pyrrole-2-acetic acid.

EXAMPLE LIII 5-(p-Chlorobenzoyl)-1-methylpyrrole-2-acetonitrile: An acylating solution is prepared by the slow addition of 278 g. (1.58 moles) of p-chlorobenzoyl chloride to 210 g. (1.58 moles) of aluminum chloride in 750 ml. of ethylene chloride. The resulting solution is added to a solution of 190 g. (1.58 moles) of N-methylpyrrole-2-acetonitrile in 750 ml. of ethylene chloride. The temperature is maintained at 20°–22°C. during the addition; and the solution is further stirred at room temperature for one hour. The solution is then heated rapidly to 74°–76°C. at which point there is a vigorous evolution of hydrogen chloride gas. This temperature is maintained about 5 minutes and the solution is cooled rapidly and poured into ice water. The product is extracted with methylene chloride and washed with water. The organic solution is then shaken with an excess of an aqueous solution of N,N-dimethylaminopropylamine followed by dilute hydrochloric acid in order to remove any excess p-chlorobenzoyl chloride. After a final wash with brine, the solution is dried over anhydrous magnesium sulfate. Distillation of the solvent leaves a residue which crystallizes. Recrystallization from methyl alcohol yields the product, 5-(p-chlorobenzoyl)-1-methylpyrrole-2-acetonitrile, m.p. 120°–124°C. After two additional recrystallizations from methanol, the m.p. is 127°–131°C.

EXAMPLE LIV 5-(p-Chlorobenzoyl)-1-methylpyrrole-2-acetic acid: A mixture of 129 g. (0.52 mole) of 5-(p-chlorobenzoyl)-1-methylpyrrole-2-acetonitrile and 88 g. (1.1 moles) of 50% sodium hydroxide solution in 800 ml. of ethanol and 500 ml. of water is stirred and refluxed for about 18 hours with slow evolution of ammonia. The solution is then cooled to about 50°C. and acidified by adding 110 ml. of concentrated hydrochloric acid. The mixture is cooled and the precipitated product, 5-(p-chlorobenzoyl)-1-methylpyrrole-2-acetic acid, is filtered and recrystallized from methanol, m.p. 193°–195°C. (dec.). A second crop is obtained upon concentration of the mother liquor for a total yield of about 67% of theoretical.

Analysis: Calcd. for $C_{14}H_{11}ClNO_3$: N, 5.05%. Found: N, 5.06%.

EXAMPLE LV

Ethyl 5-(p-chlorobenzoyl)-1-methyl-pyrrole-2-acetate: A suspension of 55.4 g. of 5-(p-chlorobenzoyl)-1-methyl-pyrrole-2-acetic acid, 44 ml. of absolute ethanol, 1g. of p-toluenesulfonic acid and 650 ml. of benzene is heated under reflux with azeotropic removal of water for 7 hours. The reaction mixture is filtered, washed with sodium bicarbonate solution, dried over anhyrous magnesium sulfate and the solvent evaporated in vacuo. The crystalline residue is recrystallized twice from cyclohexane to give ethyl 5-(p-chlorobenzoyl)-1-methyl-pyrrole-2-acetate as a yellow solid, m.p. 74°–76°C.

EXAMPLE LVI

The procedure of Example LV is repeated except that an equivalent amount of isopropanol and n-butanol are used in place of the ethanol used therein to yield, as respective products, the corresponding isopropyl and n-butyl esters of 5-(p-chlorobenzoyl)-1-methyl-pyrrole-2-acetate.

EXAMPLE LVII

A. Methyl 1-methylpyrrole-2-acetate: Four hundred and 50 ml. of ethereal diazomethane [prepared from 43 g. (0.2 mole) of N-methyl-N-nitroso-p-toluenesulfonamide by the method described in Organic Synthesis, Vol. IV, John Wiley & Sons, p. 250–252, (1963] is added dropwise to a cooled solution of 18.1 g. (0.13 mole) 1-methylpyrrole-2-acetic acid in 100 ml. of anhydrous methanol keeping the temperature at approximately 0°C. When the evolution of gas ceases, the mixture is washed three times with saturated sodium bicarbonate solution, once with saturated sodium chloride solution, and dried over anhydrous magnesium sulfate. The solvent is evaporated, yielding about 14.5 g. of an oily residue of methyl 1-methylpyrrole-2-acetate which is used without further purification in the procedure of Example LVIII-A.

B. Methyl pyrrole-2-acetate is obtained by repeating the procedure of Example LVII-A, except that an equivalent quantity of pyrrole-2-acetic acid is used in place of the 1-methylpyrrole-2-acetic acid used therein.

EXAMPLE LVIII

A. Methyl 5-(p-chlorobenzoyl)-1-methylpyrrole-2-acetate: Ten and a half grams of p-chlorobenzoyl chloride is added dropwise to a chilled suspension of 8 g. (0.06 mole) of aluminum chloride in 60 ml. of methylene chloride. The resulting solution is added quickly but dropwise to a solution of 7.6 g. (0.05 mole) methyl 1-methylpyrrole-2-acetate in 30 ml. of methylene chloride keeping the temperature below 10°C. The reaction mixture is stirred for 20 minutes, then poured into 3N hydrochloric acid, and the resulting mixture extracted with ether. The ether fraction is washed successively with N,N-dimethyl-1,3-propanediamine, with 3N hydrochloric acid and with saturated sodium chloride solution, and then dried over anhydrous magnesium sulfate. The solvent is evaporated in vacuo and the resulting solid, methyl 5-(p-chlorobenzoyl)-1-methyl-pyrrole-2-acetate, is purified by recrystallization from methanol, m.p. 122°–125°C.

B. Methyl 5-(p-chlorobenzoyl)-pyrrole-2-acetate is obtained by repeating the procedure of Example LVIII-A, except that an equivalent quantity of methyl pyrrole-2-acetate is used in place of the methyl 1-methyl-pyrrole-2-acetate used therein.

EXAMPLE LIX

By repeating the procedures of Example LVIII (A and B), except that an equivalent quantity of an appropriate benzoyl chloride is used in place of the p-chlorobenzoyl chloride used therein, the following respective products are obtained:
methyl 5-benzoyl-pyrrole-2-acetate;
methyl 5-benzoyl-1-methylpyrrole-2-acetate;
methyl 5-(p-bromobenzoyl)-1-methylpyrrole-2-acetate;
methyl 5-(p-methoxybenzoyl)-1-methylpyrrole-2-acetate; and
methyl 5-(2',4'-dichlorobenzoyl)-pyrrole-2-acetate.

EXAMPLE LX 5-(p-Chlorobenzoyl)-1-methylpyrrole-2-acetamide: A mixture of 12.4 g. (0.05 mole) of 5-(p-chlorobenzoyl)-1-methylpyrrole-2-acetonitrile and 8 g. of 50% sodium hydroxide solution in 50 ml. of water and 75 ml. of methyl alcohol is stirred and refluxed for 45 minutes. The resulting solid is filtered from the hot solution and recrystallized from dimethyl formamide to give about 8.5 g. (62%) of the product 5-(p-chlorobenzoyl)-1-methylpyrrole-2-acetamide, m.p. 250°–253°λ C.(dec.).

Analysis: Calcd. for $C_{14}H_{13}ClN_2O_2$: N, 10.13%. Found: N, 9.97%.

EXAMPLE LXI

The procedure of Example LX is followed to hydrolyze the cyano function of the subject compounds to an amide function (i.e., "$R_2$"). For example, by repeating said procedure with an equivalent amount of an appropriate 5-aroyl-1-$R_1$-2-alkanonitrile as the starting material, the following respective products are obtained:
5-benzoyl-1-methylpyrrole-2-acetamide;
5-(p-chlorobenzoyl)-pyrrole-2-acetamide;
5-(3'-chloro-p-toluoyl)1-methylpyrrole-2-acetamide;
5-(p-methoxybenzoyl)-pyrrole-2-acetamide;
5-(p-chlorobenzoyl)-1-ethylpyrrole-2-acetamide; and
1-benzyl-5-(p-chlorobenzoyl)-pyrrole-2-acetamide.

EXAMPLE LXII 5-(p-Chlorobenzoyl)-N-ethyl-1-methylpyrrole-2-acetamide: A suspension of 6.0 g. (0.02 mole) of the sodium salt of 5-(p-chlorobenzoyl)-1-methylpyrrole-2-acetic acid in 100 ml. of dry benzene is treated with 2.1 ml. (0.025 mole) of oxalyl chloride in 100 ml. benzene. The mixture is stirred for 3 hours, filtered, evaporated in vacuo and the residue taken up in benzene. The benzene mixture is poured into 50 ml. of 70% ethylamine in 200 ml. of water. The precipitated solid is filtered and dried. It is recrystallized from ethanol to give about 2.0 g. of 5-(p-chlorobenzoyl)-N-ethyl-1-methylpyrrole-2-acetamide as white needles, m.p. 187°–188°C.

Analysis: Calcd. for $C_{16}H_{17}ClN_2O_2$: C, 63.05; H, 5.62; N, 9.20%. Found: C, 63.06; H, 5.61; N, 9.14%.

EXAMPLE LXIII 5-(p-Chlorobenzoyl)-N,N-diethyl-1-methylpyrrole-2-acetamide: To a solution of 6.1 g. (0.02 mole) of 5-(p-chlorobenzoyl)-1-methylpyrrole-2-acetic acid in 100 ml. chloroform is added 3.8 ml. (0.03 mole) thionyl chloride. The mixture is stirred and refluxed overnight. The solvent is then evaporated and the residue is added quickly to a solution of 22 ml. diethylamine in 50 ml. water while cooling externally with an ice-bath. A solid precipitates, 5-(p-chlorobenzoyl)-N,N-diethyl-1-methylpyrrole-2-acetamide, which is collected and purified by recrystallization from methylcyclohexane (with charcoal while in solution), m.p. 82°–85°C.

Analysis: Calcd. for $C_{16}H_{17}ClN_2O_2$: C, 6305; H, 5.62; N, 9.20%. Found: C, 63.06; H, 5.61; N, 9.14%.

EXAMPLE LXIV

By following the respective procedures of Examples LXII and LXIII, except that an equivalent amount of an appropriate 5-aroyl-pyrrole-2-alkanoic acid or salt thereof and an equivalent quantity of an appropriate primary or secondary alkylamine are used as starting materials, the following respective products are obtained:
5-benzoyl-N-ethyl-1-methylpyrrole-2-acetamide;
5-benzoyl-N,N-diethyl-pyrrole-2-acetamide;
1-benzyl-5-(p-chlorobenzoyl)-N-isopropyl-pyrrole-2-acetamide;
5-(p-toluoyl)-N,N-dimethyl-1-methylpyrrole-2-acetamide;
5-(p-chlorobenzoyl)-1-ethyl-N-(n-butyl)-pyrrole-2-acetamide; and
5-(p-chlorobenzoyl)-N-ethyl-α-methyl-1-methylpyrrole-2-acetamide.

EXAMPLE LXV

The procedure described by R. Jones and J. Lindner in the Canadian Journal of Chemistry, 18, 883 (1965), wherein N-alkylpyrrole-2-carboxyaldehydes are reacted with ethoxycarbonylmethylene triphenylphosphorane to yield ethyl 2-(1-alkyl-2-pyrrolyl)-acrylates, is followed to prepare, as respective products, the 1-methyl, 1-(n-butyl) and 1-isoamyl derivatives of ethyl 2-(2-pyrrolyl)-acrylate.

EXAMPLE LXVI

Ethyl 2-(1-methyl-2-pyrrolyl)-propionate: A solution of 62.4 g. (0.35 mole) ethyl 2-(1-methyl-2-pyrrolyl)-acrylate in 350 ml. 95% ethanol is hydrogenated in a Parr shaker using 3 g. of platinum oxide as the catalyst. The hydrogenation is continued overnight under 32 p.s.i. of hydrogen. The mixture is filtered and the filtrate concentrated in vacuo. The residual yellow oil is dissolved in ether and washed successively with 3N hydrochloric acid, saturated sodium bicarbonate solution and saturated sodium chloride solution. The ether solution is dried over anhydrous magnesium sulfate. The ether solvent is then evaporated to yield about 42 g. of a clear oil, ethyl 2-(1-methyl-2-pyrrolyl)-propionate.

EXAMPLE LXVII

Ethyl 5-(p-chlorobenzoyl)-1-methylpyrrole-2-propionate: To a suspension of 26.6 g. (0.2 mole) of aluminum chloride in 100 ml. methylene chloride is added 34.8 g. (0.2 mole) of p-chlorobenzoyl chloride. The resulting solution is added dropwise to a solution of 36.8 g. (0.2 mole) of ethyl 2-(1-methyl-2-pyrrolyl)-propionate in 100 ml. methylene chloride while cooling externally with an ice bath. After the addition is complete, the reaction is stirred for 10 minutes and poured into ice acidified with dilute hydrochloric acid. The two fractions are separated. The organic fraction is washed successively with N,N-dimethyl-1,3-propanediamine, 3N hydrochloric acid, saturated sodium bicarbonate solution and saturated sodium chloride solution. The organic fraction is then dried over anhydrous magnesium sulfate and the solvent evaporated in vacuo. A solid is crystallized in the resulting oily residue which is isolated and purified by recrystallization from methanol to yield ethyl 5-(p-chlorobenzoyl)-1-methylpyrrole-2-propionate, m.p. 71.5°–73°C.

EXAMPLE LXVIII 5-(p-Chlorobenzoyl)-1-methylpyrrole-2-propionic acid: A suspension of 8.0 g. (0.025 mole) of ethyl 5-(p-chlorobenzoyl)-1-methylpyrrole-2-propionate in 15 ml. ethanol and 30 ml. 1N sodium hydroxide is refluxed for 1 hour. The ethanol is then evaporated and the remaining solution is poured into dilute hydrochloric acid. The resulting white precipitate is filtered off and purified by recrystallization from isopropyl alcohol, 5-(p-chlorobenzoyl)-1-methylpyrrole-2-propionic acid, m.p. 188°–191°C.

EXAMPLE LXIX

The successive procedures of Examples LXVI, LXVII and LXVIII are repeated, except that an equivalent amount of the 1-(n-butyl) and 1-isoamyl derivative of ethyl 2-(2-pyrrolyl)-acrylate is used initially, to yield, as respective products:
ethyl 2-(1-n-butyl-2-pyrrolyl)-propionate;
ethyl 2-(1-isoamyl-2-pyrrolyl)-propionate;
ethyl 5-(p-chlorobenzoyl)-1-N-butylpyrrole-2-propionate;
ethyl 5-(p-chlorobenzoyl)-1-isosmylpyrrole-2-propionate;
5-(p-chlorobenzoyl)-1-n-butylpyrrole-2-propionic acid; and
5-(p-chlorobenzoyl)-1-isoamylpyrrole-2-propionic acid.

EXAMPLE LXX

A. The acylation procedure of Example LXVII is repeated, except that an equivalent amount of an appropriate ethyl 2-(1-alkyl-2-pyrrolyl)-propionate and an equivalent amount of an appropriate benzoyl chloride acylating agent are employed, to yield as respective products:
ethyl 5-(p-methylbenzoyl)-1-methylpyrrole-2-propionate;
ethyl 5-(p-ethoxybenzoyl)-1-n-butylpyrrole-2-propionate;
ethyl 5-(2',4'-dichlorobenzoyl)-1-methylpyrrole-2-propionate;
ethyl 5-(p-cyanobenzoyl)-1-isoamylpyrrole-2-propionate;
ethyl 5-(p-methylthiobenzoyl)-1-methylpyrrole-2-propionate;
ethyl 5-(p-nitrobenzoyl)-1-methylpyrrole-2-propionate;
ethyl 5-(3',4',5'-trimethoxybenzoyl)-1-methylpyrrole-2-propionate;
ethyl 5-thenoyl-1-methylpyrrole-2-propionate;
ethyl 5-(5-methylthenoyl)-1-methylpyrrole-2-propionate; and
ethyl 5-(p-trifluoromethylbenzoyl)-1-methylpyrrole-2-propionate.

B. The ester-to-acid transformation procedure of Example LXVIII is repeated using an equivalent amount of each propionate ester obtained from Example LXX-A in place of the ester used therein to yield, as respective products, the corresponding 5-aroyl-1-alkyl-pyrrole-2-propionic acid.

C. By using an equivalent amount of ethyl 5-(p-nitrobenzoyl)-1-methylpyrrole-2-propionate in place of 5-(p-nitrobenzoyl)-1-methylpyrrole-2-acetonitrile in the hydrogenation procedure of Example XXIV, the product, ethyl 5-(p-aminobenzoyl)-1-methylpyrrole-2-propionate is obtained. Conventional ammonolysis of the latter ester with ammonia or treatment with a primary or secondary lowe alkylamine affords the corresponding propionamides.

D. By repeating the hydrolysis procedure of Example LXVIII with an equivalent amount of the ester obtained from Example LXX-C in place of the ester used therein, the product, 5-(p-aminobenzoyl)-1-methylpyrrole-2-propionic acid is obtained.

EXAMPLE LXXI

The procedure described by Ceresole in Ber., 17, 815 (1884), wherein 1-aryl-1,3-butanediones are reacted with nitrous acid to yield the corresponding 1-aryl-1,2,3-butanetrione-2-oximes, is followed to prepare, as respective products:
1-phenyl-1,2,3-butanetrione-2-oxime, m.p. 130°–131°C.;
1-p-chlorophenyl-1,2,3-butanetrione-2-oxime;
1-p-methylphenyl-1,2,3-butanetrione-2-oxime; and
1-p-methoxyphenyl-1,2,3-butanetrione-2-oxime.

EXAMPLE LXXII

A. Ethyl 5-benzoyl-3-ethoxycarbonyl-4-methylpyrrole-2-acetate: A solution of 71 g. (0.37 mole) of 1-phenyl-1,2,3-butanetrione-2-oxime in 350 ml. glacial acetic acid and 50 ml. of water is added to 75.5 g. diethyl acetonedicarboxylate in 350 ml. of glacial acetic acid at 70°C. Concurrently, a mixture of 73 g. (1.12 mole) of zinc dust and 91.5 g. (1.12 mole) of anhydrous sodium acetate is added in portions at such a rate that the temperature is maintained near 100°C. After the additions are complete (about 45 minutes), the mixture is refluxed for one hour and poured into iced water. The resulting crude semisolid is collected by filtration and recrystallized twice from methanol to give ethyl 5-benzoyl-3-ethoxycarbonyl-4-methylpyrrole-2-acetate, m.p. 152°–154°C.
Analysis: Calcd. for $C_{19}H_{21}NO_5$: C, 66.46; H, 6.16; N, 4.08%. Found: C, 66.50; H, 6.20; N, 4.17%.

B. By repeating the procedure of Example LXXII-A with an equivalent amount of the 1-p-chlorophenyl, 1-p-methylphenyl and 1-p-methoxyphenyl derivative of 1,2,3-butanetrione-2-oxime, there are obtained as respective products, the corresponding ethyl 5-aroyl-3-ethoxycarbonyl-4-methylpyrrole-2-acetates.

EXAMPLE LXXIII

A. 5-Benzoyl-3-carboxy-4-methylpyrrole-2-acetic acid: A mixture of 3.4 g. of ethyl 5-benzoyl-3-ethoxycarbonyl-4-methylpyrrole-2-acetate, 10 g. of 50% sodium hydroxide solution and 10 ml. of water is refluxed for 2 hours. The reaction mixture is then diluted with water and acidified with dilute hydrochloric acid. The precipitated solid is collected by filtration, air-dried, and recrystallized from acetone-water to yield the product, 5-benzoyl-3-carboxy-4-methylpyrrole-2-acetic acid, as white crystals, m.p. 250°–253°C.

B. The hydrolysis procedure of Example LXXIII-A is repeated, except that an equivalent amount of each ester obtained in Example LXXII-B is used, to yield, as respective products, the corresponding 5-p-chlorobenzoyl, 5-p-methylbenzoyl and 5-p-methoxybenzoyl derivatives of 3-carboxy-4-methylpyrrole-2-acetic acid.

EXAMPLE LXXIV

A. Ethyl 5-benzoyl-3-carboxy-4-methylpyrrole-2-acetate: A solution of 8.0 g. (0.028 mole) of 5-benzoyl-3-carboxy-4-methylpyrrole-2-acetic acid in 80 ml. of 0.5% ethanolic hydrogen chloride is refluxed for 90 minutes. The solution is charcoaled, filtered, and the filtrate evaporated in vacuo to yield a crystalline residue which is recrystallized from acetone to give ethyl 5-benzoyl-3-carboxy-4-methylpyrrole-2-acetate, m.p. 183°–185°C.

B. The partial reesterification procedure of Example LXIV-A is repeated using an equivalent amount of the respective acids obtained in Example LXXIII-B to yield the corresponding ethyl 5-aroyl-3-carboxy-4-methyl-pyrrole-2-acetates, respectively.

EXAMPLE LXXV

A. 5-Benzoyl-4-methylpyrrole-2-acetic acid: A solution of 4.13 g. (0.0131 mole) of ethyl 5-benzoyl-3-carboxy-4-methyl-pyrrole-2-acetate in 80 ml. of quinoline in the presence of a trace amount of copper chromite is heated at 180°–183°C for 5 hours. The mixture is poured into dilute hydrochloric acid and extracted three times with ether. The ether extracts are combined and washed successively with dilute hydrochloric acid, sodium bicarbonate solution and brine and then dried over anhydrous magnesium sulfate. The solvent is evaporated in vacuo to give about 4 g. of semisolid ethyl 5-benzoyl-4-methylpyrrole-2-acetate which is used in the following hydrolysis procedure without further purification.

The entire semisolid is dissolved in 20 ml. of ethanol and 20 ml. of 1N sodium hydroxide solution is added. The mixture is heated under reflux for 30 minutes. The solvent is then evaporated in vacuo and the residue dissolved in water and washed with ether. The aqueous solution is acidified with dilute hydrochloric acid and the resulting crystalline solid (1.6 g., 50% yield) is collected by filtration and air-dried. The product, 5-benzoyl-4-methylpyrrole-2-acetic acid. is recrystallized three times from acetone-water with charcoaling, m.p. 167°–168°C.

B. The procedure of Example LXXV-A is repeated using an equivalent amount of the respective esters obtained in Example LXXIV-B to yield the corresponding 5-p-chlorobenzoyl, 5-p-methylbenzoyl and 5-p-methoxybenzoyl derivatives, respectively, of 4-methylpyrrole-2-acetic acid.

C. Lower alkyl esters of the acids obtained in A and B of this Example, such as, for example, the ethyl, isopropyl and n-butyl esters, are prepared by conventional esterification techniques using an appropriate lower alkanol.

D. Primary, secondary and tertiary amides of the acids obtained in A and B of this Example are prepared by conventional procedures, for example, by treatment with thionyl chloride and then contacting the thus-obtained acid chloride with ammonia, a primary lower alkylamine or a secondary lower alkylamine, such as:
5-benzoyl-N,N-diethyl-4-methylpyrrole-2-acetamide;
5-(p-chlorobenzoyl)-4-methylpyrrole-2-acetamide;
5-(p-methylbenzoyl)-N-methyl-4-methylpyrrole-2-acetamide; and
5-(p-methoxybenzoyl)-N-ethyl-4-methylpyrrole-2-acetamide.

EXAMPLE LXXVI

A. Ethyl 5-(p-chlorobenzoyl)-2,4-dimethylpyrrole-3-acetate: To a solution of 29 g. (0.17 mole) of p-chlorobenzoyl chloride and 28.0 g. (0.15 mole) of ethyl 2,4-dimethylpyrrole-3acetate in 100 ml. carbon disulfide, is added 41.23 g. (0.31 mole) of anhydrous aluminum chloride. The reaction mixture is cooled externally with a ice bath. The mixture is stirred for 15 minutes after which the solvent is decanted and the remaining solid treated with ice acidified with 3N hydrochloric acid. The acidic mixture is extracted three times with ether. The combined ether extracts are washed successively with N,N-dimethyl-1,3-propanediamine, 3N hydrochloric acid, and a saturated solution of sodium chloride. The solution is dried over anhydrous magnesium sulfate and the solvent evaporated in vacuo. The remaining solid is recrystallized from methanol to yield, ethyl 5-(p-chlorobenzoyl)-2,4-dimethylpyrrole-3-acetate, m.p. 126°–129°C.

B. By repeating the procedure of Example LXXVI-A, except that an equivalent amount of an appropriate benzoyl chloride is used as the acylating agent, there are obtained as respective products:
ethyl 5-benzoyl-2,4-dimethylpyrrole-3-acetate;
ethyl 5-(p-methoxybenzoyl)-2,4-dimethylpyrrole-3-acetate;
ethyl 5-(2',4'-dichlorobenzoyl)-2,4-dimethylpyrrole-3-acetate;
ethyl 5-(3'-chloro-4'-methylbenzoyl)-2,4-dimethylpyrrole-3-acetate

EXAMPLE LXXVII

A. Ethyl 5-(p-chlorobenzoyl)-4-methyl-2-trichloromethylpyrrole-3-acetate: To a suspension of 9.6 g. (0.03 mole) of ethyl 5-(p-chlorobenzoyl)-2,4-dimethylpyrrole-3-acetate in 75 ml. ether is added dropwise 7.8 ml. sulfurylchloride, cooling externally with an ice bath. The resulting suspension is stirred at room temperature for 15 hours. The resulting white solid, ethyl 5-(p-chlorobenzoyl)-4-methyl-2-trichloromethylpyrrole-3-acetate, is filtered and purified by recrystallization twice from methylcyclohexane, m.p. 133°–137°C.

B. Perchlorination of the 2-methyl group in the esters obtained from Example LXXVI-B is performed by repeating the procedure of Example LXXVII-A.

EXAMPLE LXXVIII

A. 5-(p-Chlorobenzoyl)-4-methyl-2-carboxypyrrole-3-acetic acid: A solution of 1.0 g. (0.0026 mole) of ethyl 5-(p-chlorobenzoyl)-4-methyl-2-trichloromethylpyrrole-3-acetate in 10 ml. dioxane and 3 ml. water is refluxed for 3 hours. The resulting solution is cooled and extracted with chloroform. The organic fraction is extracted with a saturated solution of sodium bicarbonate. The aqueous phase is made acidic with dilute hydrochloric acid and the resulting precipitate of 5-(p-chlorobenzoyl)-4-methyl-2-carboxypyrrole-3-acetic acid is filtered and dried, m.p. 240°C.

B. The procedure of Example LXXVIII-A is repeated using an equivalent amount of the 2-trichloromethyl esters obtained from Example LXXVII-B to yield, as respective products, the corresponding 5-aroyl-4-methyl-2-carboxypyrrole-3-acetic acids.

EXAMPLE LXXIX

A. 5-(p-Chlorobenzoyl)-4-methylpyrrole-3-acetic acid: A solution of 1.4 g. (0.004 mole) of 5-(p-chlorobenzoyl)-4-methyl-2-carboxypyrrole-3-acetic acid in 25 ml. quinoline is heated overnight at 160°C. under nitrogen. The reaction is poured into ice acidified with hydrochloric acid. The mixture is extracted with chloroform and the organic phase is extracted with a saturated solution of sodium bicarbonate. The basic solution is made acidic with dilute hydrochloric acid and the resulting solid, 5-(p-chlorobenzoyl)-4-methylpyrrole-3-acetic acid, is filtered and purified by recrystallization from isopropyl alcohol, m.p. 145°–147°C.

B. The decarboxylation procedure of Example LXXIX-A is repeated, except that an equivalent amount of the 2-carboxypyrrole-3-acetic acids obtained in Example LXXVIII-B is used as the starting acid, to yield the corresponding 5-aroyl-4-methylpyrrole-3-acetic acids, respectively.

C. Lower alkyl esters of the acids obtained in A and B of this Example, such as, for example, the ethyl, isopropyl and n-butyl esters, are prepared by conventional esterification procedures using an appropriate lower alkanol.

D. Primary, secondary and tertiary amides of the acids obtained in A and B of this Example are prepared by conventional procedures to yield, for example, the following respective amides:
5-(p-chlorobenzoyl)-4-methylpyrrole-3-acetamide;
5-benzoyl-N-ethyl-4-methylpyrrole-3-acetamide;
5-(p-methoxybenzoyl)-N-n-propyl-4-methylpyrrole-3-acetamide;
5-(2',4'-dichlorobenzoyl)-N,N-diethyl-4-methylpyrrole-3-acetamide

EXAMPLE LXXX

A. 2-Dimethylaminomethyl-1-benzylpyrrole: A solution of 8.2 g. (0.1 mole) dimethylamine hydrochloride in 8 ml. formalin is added dropwise to 17.12 g. (0.1 mole) of 1-benzylpyrrole. The mixture is stirred at room temperature until solution occurs (about 4 hours). The solution is poured into 10% sodium hydroxide solution and then extracted into ether three times. The combined organic fractions are washed with a saturated solution of sodium chloride, dried over magnesium sulfate and the solvent evaporated in vacuo. The product, 2-dimethylaminomethyl-1-benzylpyrrole, is distilled at reduced pressure, b.p. 73°C., 0.025 mm. Hg.

B. 2-Dimethylaminomethyl-1-benzylpyrrole methiodide: A solution of 100 g. (0.47 mole) of 2-dimethylaminomethyl-1-benzylpyrrole in 200 ml. of absolute ethanol is cooled to 5°C. To this is added dropwise 29.4 ml. (0.47 mole) of methyl iodide. A white solid precipitates. The suspension is stirred until the precipitate is so thick that additional stirring becomes impossible. The solid, 2-dimethylaminomethyl-1-benzylpyrrole methiodide, is filtered off and dried in vacuum.

C. 1-Benzylpyrrole-2-acetonitrile: A suspension of 88.9 g. (0.25 mole) of 2-dimethylaminomethyl-1-benzylpyrrole methiodide is added to a suspension of 12.8 g. (0.26 mole) of sodium cyanide in 40 ml. dimethylsulfoxide. The mixture is heated under reflux for 3 hours and stirring at room temperature is continued overnight. The reaction mixture is poured into water and extracted three times with ether. The combined ether extracts are washed with brine and dried over anhydrous magnesium sulfate. The ether solvent is evaporated in vacuo to give about 41 g. of an oily residue which crystallizes upon standing. Recrystallization from methylcyclohexane yields the product, 1-benzylpyrrole-2-acetonitrile, m.p. 62°-63°C.

EXAMPLE LXXXI

A. 3-Chloro-4-methylbenzoyl chloride is prepared by refluxing together 30 g. (0.175 mole) of 3-chloro-4-methyl benzoic acid and 85 ml. thionyl chloride for about 2.5 hours, after which the excess thionyl chloride is distilled off under vacuum. The aroyl chloride product, 3-chloro-4-methylbenzoyl chloride, distills over at b.p. 70°-74°C., 10.25 mm. Hg.

B. The procedure of Example LXXXI-A represents a method for transforming benzoic acid derivatives to the corresponding acid chloride form. By following such procedure, except that an equivalent amount of an appropriately substituted benzoic acid is initially employed, the following aroyl chlorides are obtained:
3,4-dimethoxybenzoyl chloride;
3-bromo-4-chlorobenzoyl chloride;
2,3,5-tribromobenzoyl chloride;
3,4-dimethylbenzoyl chloride;
p-ethylbenzoyl chloride;
p-ethoxybenzoyl chloride; and
p-methylthiobenzoyl chloride.

EXAMPLE LXXXII

Primary, secondary and tertiary amides of the acids obtained in Examples LXVIII, LXIX, LXX-B and LXX-D are prepared by conventional treatment of the corresponding acid chloride with ammonia or an appropriate alkylamine or dialkylamine to yield, for example, the following respective amides:
5-(p-chlorobenzoyl)-1-methylpyrrole-2-propionamide;
5-(p-chlorobenzoyl)-1-n-butylpyrrole-2-propionamide;
5-(p-chlorobenzoyl)-1-isoamylpyrrole-2-propionamide;
5-(p-methylbenzoyl)-N-ethyl-1-methylpyrrole-2-propionamide;
5-(3',4',5'-trimethoxybenzoyl)-N,N-diethyl-1-methylpyrrole-2-propionamide; and
5-(p-nitrobenzoyl)-1-methylpyrrole-2-propionamide.

EXAMPLE LXXXIII

A. 1-Benzyl-5-(p-chlorobenzoyl)-pyrrole-2-acetonitrile: A solution of 8.43 ml. (0.067 mole) of p-chlorobenzoyl chloride and 8.8 g. (0.067 mole) of aluminum chloride in 100 ml. of 1,2-dichloroethane is added to a solution of 13.0 g. (0.067 mole) of 1-benzylpyrrole-2acetonitrile in 50 ml. of 1,2-dichloroethane at 5°C. over a 5 minute period. The reaction mixture is stirred for 15 minutes and then heated quickly to reflux for 3 minutes. The mixture is poured into ice-hydrochloric acid and then filtered. The aqueous layer is separated and washed with chloroform. The combined organic fractions are washed successively with N,N-dimetylaminopropylamine solution, dilute hydrochloric acid and brine and then dried over anhydrous magnesium sulfate. The solvent is evaporated to yield an oily residue from which the desired compound is isolated by column chromatography on neutral alumina with a 50–50 mixture of benzeneether as the eluting solvent. Evaporation of the elute affords 1-benzyl-5-(p-chlorobenzoyl)-pyrrole-2-acetonitrile as a yellow solid which is recyrstallized from methanol, m.p. 106°-108° C,.

B. 1-Benzyl-4-(p-chlorobenzoyl)-pyrrole-2-acetonitrile: Continued elution of the column in Example LXXXIII-A with ethyl acetate, followed by evaporation of the eluate yields a yellow oil which crystallizes from benzene-methylcyclohexane to yield 1-benzyl-4(p-chlorobenzoyl)-pyrrole-2-acetonitrile as a white solid, m.p. 102°-104°C.

EXAMPLE LXXXIV 5-(p-Isopropylbenzoyl)-1-methylpyrrole-2-acetonitrile: To a suspension of 17.5 g. (0.131 mole) aluminum chloride in 60 ml. 1,2-dichloroethane is added 24 g (0.131 mole) p-isopropylbenzoyl chloride. The resulting mixture is added slowly and dropwise to a chilled solution (0°C.) of 15.7 g. (0.131 mole) 1-methylpyrrole-2-acetonitrile in 100 ml. of 1,2-dichloroethane. After addition is complete, the mixture is stirred at room temperature for twenty minutes and heated at reflux for three minutes. The reaction mixture is then cooled and poured into ice-dilute hydrochloric acid. The organic phase is separated and washed successively with N,N-dimethyl-1,3-propanediamine, dilute hydrochloric acid and a saturated solution of sodium chloride; dried over magnesium sulfate; and the solvent evaporated. The product, 5-(p-isopropylbenzyl)-1-methylpyrrole-2-acetonitrile, is isolated from the residual oil by column chromatography. The column is packed with acid washed alumina and eluted with benzene, ether and etylacetate. The product is found in the first compound-bearing fraction which absorbs ultraviolet light at approximately 250 m$\mu$. It is purified by recrystallization twice in ether: pentane (7g.; 20% yield). m.p. 59°–64°C.

Anal. Calcd. for $C_{17}H_{18}N_2O$: N, 10.53%. Found: N10.71%.

EXAMPLE LXXXV 5-(p-Isopropylbenzoyl)-1-methylpyrrole-2-acetic acid: A solution of 6.5 g. (0.024 mole) of 5-(p-isopropylbenzoyl)-1-methylpyrrole-2-acetonitrile, 52 ml. 1N sodium hydroxide and 50 ml. 95% ethanol are heated at reflux overnight. The ethanol is then evaporated and the remaining yellow solution is poured into ice-dilute hydrochloric acid. A precipitate forms which is separated by filtration and recrystallized in ether: hexane. The solid is then partitioned between sodium bicarbonate solution and ether. The sodium bicarbonate phase is separated and acidified with dilute hydrochloric acid. The wite precipitate, 5-(p-isopropylbenzoyl)-1methylpyrrole-2-acetic acid, is filtered and dried in vacuo (4.0 g., 58% yield), 98°–101°C.

Anal. Calcd. for $C_{17}H_{19}NO_3$: N, 4.91%. Found: N, 5.14%.

EXAMPLE LXXXVI

1-Methyl-5-(o-toluoyl)-pyrrole.-2-acetonitrile: To a solution of 24 g. (0.20 mole) of 1-methylpyrrole-2-acetonitrile and 30.92 g. (0.20 mole) o-toluoyl chloride in 200 ml. methylene chloride (cooled externally to −20°C.) is added dropwise 23.4 ml. (0.20 mole) of stannic chloride. After the addition is complete, the yellow mixture is permitted to come to room temperature. The mixture is then poured into ice-dilute hydrochloric acid. The two phases are separated. The organic phase is washed consecutively with N,N-dimetyl-1,3-propanediamine, 3N hydrochloric acid, and saturated sodium chloride solution; dried over magnesium sulfate; and the product, 1-methyl-5-(o-toluoyl)-pyrrole-2-acetonitrile, is separated from the residual oil by chromatography. The column is packed with acid washed alumina in hexane. The eluant is benzene. The product is found in the first compoundbearing fraction as determined by ultraviolet absorption at 260 m$\mu$. The benzene is evaporated and the resultant solid is purified by recrystallization twice from methaol, m.p. 90°–92.5°C.

EXAMPLE LXXXVII

1-Methyl-5-(o-toluoyl)-pyrrole-2-acetic acid: A solution of 10.6 g. (0.0445 mole) of 1-methyl-5-(o-toluoyl)-pyrrole-2-acetonitrile, 89 ml. 1N sodium hydroxide and 10 ml. 95% ethanol is heated at reflux for 18 hours, cooled and poured into dlute hydrochloric acid, and extracted with chloroform. The chloroform phase is separated and extracted with sodium bicarbonate solution. The product, 1-methyl-5-(o-toluoyl)-pyrrole-2-acetic acid, is precipitated from the aqueous phase upon treatment with 3N hydrochloric acid, separated by filtration, and purified by recrystallization in isopropanol using charcoal while the solution is still warm, and subsequent recrystallization with methanol, m.p. 133°–135°C.

Anal. Calcd. for $C_{15}H_{15}NO_3$: C, 70.02; H, 5.88; N, 5.44%. Found: C, 70.07; H, 5.97; N, 5.54%.

EXAMPLE LXXXVIII

1-Methyl-5-(2-thenoyl)-pyrrole-2-acetonitrile: A solution of 20.0 g. (0.15 mole) of aluminum chloride and 22.0 g. (0.15 mole) of thiophene-2-carboxylic acid chloride in 200 ml. 1,2-dichloroethane is added to a solution of 18.0 g. (0.15 mole) of 1-methyl-pyrrole-2-acetonitrile in 100 ml. of 1,2-dichloroethane at 5°C. over a period of 5 min. The mixture is stirred for 20 min. and then quickly heated to reflux for 3 min. It was poured into ice-hydrochloric acid. The organic layer is separated and the aqueous solution washed with 1,2-dichloroethane. The combined organic solutions are washed consecutively with water, N,N-dimethylaminopropylamine, dilute hydrochloric acid and brine. The solution is then dried over magnesium sulfate and the solvent evaporated in vacuo. The residue crystallizes to give about 30 g. of a yellow solid which shows two spots on thin layer chromatography (1:1 ethyl acetate, cyclohexane on silica gel). The solid is dissolved in benzene and seeded with crystals of 1-methyl-4-(2-thenoyl)-pyrrole-2-acetonitrile which were obtained by exhaustive crystallization of a previous run from benzene. After crystallization, the supernatant liquid is decanted from the precipitated 1-methyl-4-(2-thenoyl)-2-acetonitrile and evaporated. The thus-obtained solid is recrystallized from methanol and seeded with crystals of 1-methyl-5-(2-thenoyl)-pyrrole-2-acetonitrile which were obtained by exhaustive crystallization of a previous run from methanol. The mother liquor from the crystallization of the latter compound is evaporated and recycled through the same crystallization processes. After four cycles, there is obtained about 7.35 g. (21%) of 1-methyl-5-(2-thenoyl)-pyrrole-2-acetonitrile, m.p. 132° –133°C.

EXAMPLE LXXXIX

1-Methyl-5-(2-thenoyl)-pyrrole-2-acetic acid: A suspension of 7.35 g. (0.032 mole) of 1-methyl-5-(2-thenoyl)-pyrrole-2-acetonitrile in 30 ml. of 95% ethanol and 64 ml. (0.064 mole) of 1N sodium hydroxide solution is refluxd for 5 hr. The mixture is cooled and the ethanol evaporated in vacuo. Water is added and the solution is washed successively with methylene chloride and ether and clarified with charcoal. The solution is acidifid with dilute hydrochloric acid and the precipitated solid, 1-methyl-5-(2-thenoyl)-pyrrole-2-acetic - acid, is collected and dried in vacuo, m.p. 140°–142°C. It is recrystallized from methanol-water to give the product as a white solid, m.p. 141°–142°C.

Anal. Calcd, for $C_{12}H_{11}NO_3S$: C, 57.83; H, 4.45; H 5.62%. Found: C, 57.81; H, 4.44; N 5.68%.

EXAMPLe XC

1-Methyl-5-(5-methyl-2-thenoyl)-pyrrole-2-acetonitrile: To a suspension of 25.54 g. (0.019 mole) anhydrous aluminum chloride in 70 ml. of 1,2-dichloroethane is added 30.7 g. (0.019 mole) 5-methyl-2-thenoyl chloride. The resulting solution is added dropwise to a chilled (0°C.) solution of 24 g. (0.02 mole) 1-methylpyrrole-2-acetonitrile. After the addition, the solution is stirred at room temperature for approximately 40 minutes and than heated at reflux for 3 minutes and poured onto ice acidified with dilute hydrochloric acid. The two phases are separated. The organic phase is washed successively with N,N-dimethyl-1,3-propanediamine, 3N hydrochloric acid and saturated sodium chloride solution. It is then dried over magnesium sulfate and the solvent evaporated. The resulting solid, 1-methyl-5-(5-methyl-2-thenoyl)-pyrrole-2-acetonitrile, is separated by filtration and purified by washing in cold methanol and benzene, m.p. 118°–121°C.

EXAMPLE XCI

1-Methyl-5-(5-methyl-2-thenoyl)-pyrrole-2-acetic acid: A solution of 10.5 g. (0.043 mole) of 1-methyl-5-(5-methyl-2-thenoyl)-pyrrole-2-acetonitrile, 86 ml. 1N sodium hydroxide and 50 ml. 95% ethanol is refluxed for 15 hours and then cooled and poured into 3N hydrochloric acid. The white precipitate 1-methyl-5-(5-methyl-2-thenoyl)-pyrrole-2-acetic acid, is collected by filtration, air dried, and recrystallized twice in acetonitrile, m.p. 152°–154°C.

Anal. Calcd. for $C_{13}H_{13}NO_3S$: C, 59.37; H, 4.98; N, 5.33. Found: C, 59.15; H, 4.99; N, 5.64.

EXAMPLE XCII

1-Methyl-5-(p-trifluoromethyl-benzoyl)-pyrrole-2acetonitrile: A solution of 14.4 g. (0.12 mole) of 1-methylpyrrole-2-acetonitrile and 25 g. (0.12 mole) of p-trifluoromethylbenzoyl chloride in 120 ml. methylene chloride is chilled to −25°C. (external bath). Then 14 ml. (0.12 mole) stannic chloride is added dropwise over a half hour. The resultant suspension is permitted to come to room temperature and then poured into ice-dilute hydrochloric acid. The aqueous phase is separated and washed successively with N,N-dimethyl-1,3-propane-diamine, 3N hydrochloric acid and a saturated solution of sodium chloride. The solvent is evaporated and the product is isolated from the residual oil by column chromatography using acid washed alumina. The solvents hexane, benzene, and other are used as eluents. The first compound-bearing fraction not giving a positive Enrlich's test (in benzene) is collected. The solvent is evaporated and the resultant solid, 1-methyl-5-(p-trifluoromethyl-benzoyl)-pyrrole-2-acetonitrile, in purified by recrystallization in isopropanol, m.p. 95°–97.5°C.

EXAMPLE XCIII

1-Methyl-5-(p-trifluoromethyl-benzoyl)-pyrrole-2acetic acid: A solution of 2.2 g. (0.0075 mole) of 1-methyl-5-)p-trifluoromethylbenzoyl)-pyrrole-2-acetonitrile, 15 ml. 95% ethanol and 15 ml. 1N sodium hydroxide is refluxed for 18 hours. The ethanol is evaporated. The resultant yellow solid is dissolved with water and poured into dilute hydrochloric acid. The resultant white precipitate 1-methyl-5-(p-trifluoromethylbenzoyl)-pyrrole-2-acetic acid, is collected by filtration and purified by recrystallization in isopropanol, m.p. 152°–154°C.

Anal. Calcd. for $C_{15}H_{12}F_3NO_3$: C, 57.88; H, 3.89; N, 4.50%. Found: C, 57.92; H, 4.12; N, 4.38%.

EXAMPLE XCIV

A. 5-(p-Chlorobenzoyl)-1-methylpyrrole-2-acetohydroxamic acid: To a sodium methoxide solution prepared by dissolving 0.74 g. (.0322 mole) of sodium in 200 ml. of methanol is added 7.8 g. (0.0268 mole) of methyl 5-(p-chlorobenzoyl)-1-methylpyrrole-2-acetate and 2.03 g. (0.029 mole) of hydroxylamine hydrochloride. The mixture is refluxed for 18 hr. Further reagent is then added as follows: to the mixture is added 1.03 g. of hydroxylamine hydrochloride and a sodium methoxide solution prepared from 0.37 g. of sodium in 25 ml. of methanol. Reflux is continued for 24 hr. About 1 ml. of acetic acid (to neutralize the formed sodium hydroxamate salt) is added and the solution is cooled. Crystallization occurs and the solid is filtered. The solid is washed with hot chloroform and recrystallized from methanol to give a light yellow solid, 5-(p-chlorobenzoyl)-1-methylpyrrole-2-acetohydroxamic cid, m.p. 195°C.

Anal. Calcd. for $C_{14}H_{13}ClN_2O_2$: C, 57.44; H, 4.47; N, 9.56%. Found: C, 57.43; H, 4.55; N, 9.48%.

B. The foregoing procedure of Example XCIV-A, which involves the interaction of a loweralkyl 5-aroyl-pyrrole-2-acetate, preferably the methyl ester, with hydroxylamine, may be followed in preparing the other novel 5-aroyl-pyrrole-2-acetohydroxamic acids of this invention (i.e., where $R_2$ in Formula I-a is COHN—OH). Thus, by using as the starting ester an equivalent amount of an appropriate methyl 5-aroylpyrrole-2-acetate, the following respective products are obtained:

5-(p-anisoyl)-1-methylpyrrole-2-acetohydroxamic acid;

5-(3'-bromo-4'-chlorobenzoyl)-1-methylpyrrole-2-acetohydiaoxamic acid;

5-(p-chlorobenzoyl)-pyrrole-2-acetohydroxamic acid;

5-benzoyl-pyrrole-2-acetohydroxamic acid;

5-(p-ethoxybenzoyl)-1-methylpyrrole-2-acetohydroxamic acid;

5-(3',4'-dimethoxybenzoyl)-1-methylpyrrole-2-acetohydroxamic acid;

5-(p-methylthiobenzoyl)-1-methylpyrrole-2-acetohydroxamine acid;

5-(p-chlorobenzoyl)-1-benzylpyrrole-2-acetohydroxamic acid; and 5-(p-chlorobenzoyl)-α-metyl-1-methylpyrrole-2-acetohydroxamic acid.

EXAMPLE XCV

A. 5-(p-Chlorobenzoyl)-N-(2-diethylaminoethyl)-1-methylpyrrole-2-acetamide: To a fresh solution of sodium methoxide (0.14 g. sodium in 105 ml. methanol) is added first 7.0 g. (.024 mole) of methyl 5-(p-chlorobenzoyl)-1-methylpyrrole-2-acetate and then 14.0 g. (.12 mole) of N,N-diethyl-1,2-diaminoethane. The solution is refluxed for 6.5 hrs. with stirring and then stirred at room temperature for 11.5 hrs. The reaction solution is then poured into about 500 ml. of ice-water and maintained at 0°C. for several hours to aid crystal formation. A pale yellow-green solid is filtered off and air-dried to give about 6.8 g. (77.6%) of the crude amide product, which is recrystallized from hexane (with hot gravity filtration) to give about 5.9 g. (65%) of 5-(p-chlorobenzoyl)-N-(2-diethylaminoethyl)-1-methylpyrrole-2-acetamide as small yellow needles, m.p. 95.0°–96.0°C.

Anal. Calcd. for $C_{20}H_{26}N_3O_2Cl$: C 63.90; H 6.97; N 11.20%. Found: C 64.01; H 7.12; N 11.24%.

B. By repeating the procedure outlined in Example XCV-A, except that equivalent quantities of an appropriate lower alkyl 5-aroyl-pyrrole-2-acetate and N,N-dialkylamino-alkylamine are used as starting materials, the following respective products are obtained:

5-(p-anisoyl)-N-(2-diethylaminoethyl)-1-methylpyrrole-2-acetamide;
5-benzoyl-N-(3-dimethylaminopropyl)-pyrrole-2-acetamide;
5-(p-chlorobenzoyl)-N-(4-diethylaminobutyl)-1-methylpyrrole-2-acetamide;
5-(2',3',5'-tribromobenzoyl)-N-(2-diethylaminoethyl)-1-methylpyrrole-2-acetamide;
5-(p-ethoxybenzoyl)-N-(2-methylethylaminoethyl)-1-methylpyrrole-2acetamide;
5-(p-methylthiobenzoyl)-N-(2-dimethylaminopropyl)-1-methylpyrrole-2-acetamide;
5-(p-chlorobenzoyl)-N-(2-diethylaminoethyl)-1-benzylpyrrole-2-acetamide; and
5-(p-chlorobenzoyl)-α-methyl-N-(2-dimethylaminoethyl)-1-methylpyrrole-2-acetamide.

EXAMPLE XCVI

Ethyl 1,4-dimethyl-3-ethoxycarbonylpyrrole-2-acetate; To a solution of 500 ml. of 25% aqueous methylamine is added 93 g. (0.46 mole) of diethyl acetonedicarboxylate. To the mixture is added 72 g. (0.782 mole) of chloroacetone over a 10 min. period. The temperature is kept below 60°C. by external cooling. After 2 hours, the mixture is poured into ice-hydrochloric acid. The solid is collected by filtration, washed with water and air dried. It is recrystallized from hexane to give ethyl 1,4-dimethyl-3-ethoxycarbonylpyrrole-2-acetate as a white solid, m.p. 71°–72°C.

Anal. Calcd. for $C_{13}H_{19}NO_4$: C, 61.64; H, 7.56; N, 5.53%. Found: C, 61.64; H, 7.64; N, 5.71%.

EXAMPLE XCVII

Ethyl 5-(p-chlorobenzoyl)-1,4 dimethyl-3ethoxycarbonylpyrrole-2-acetate: A solution of 17.5 g. (0.1 mole) p-chlorobenzoyl chloride and 13.3 g. (0.1 mole) aluminum chloride in 150 ml. of dichloroethane is added rapidly to a solution of 25.3 g. (0.1 mole) of ethyl 1,4-dimethyl-3ethoxycarbonylpyrrole-2-acetate in 100 ml. of refluxing 1,2-dichloroethane. The solution is refluxed for 3.5 hours and poured into ice-hydrochloric acid. The organic layer is separated and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residue product is crystallized from cyclohexane and recrystallized from methanol to give ethyl 5-(p-chlorobenzoyl)-1,4 dimethyl-3-ethoxycarbonylpyrrole-2-acetate as a white solid, m.p. 91°–93°C.

EXAMPLE XCVIII 5-(p-chlorobenzoyl)-3-carboxy-1,4-dimethylpyrrole-2-acetic acid: A suspension of 17.3 g. (0.0435 mole) of ethyl 5-(p-chlorobenzoyl)-1,4 dimethyl-3-ethoxypyrrole-2-acetate in 170 g. of 25% sodium hydroxide is heated under reflux for 3 hrs. The suspension is poured into ice and the resulting yellow solution is added to ice-hydrochloric acid with stirring. The precipitated solid is collected by filtration, air dried and recrystallized from acetone containing 10% water to give 5-(p-chlorobenzoyl)-3-carboxy-1,4-dimethylpyrrole-2-acetic acid as a white solid, m.p. 253°–254°C.

EXAMPLE XCIX

Ethyl 5-(p-chlorobenzoyl)-3-carboxy-1,4dimethylpyrrole-2-acetate: A suspension of 2.0 g. of 5-(p-chlorobenzoyl)-3-carboxy-1,4-dimethylpyrrole-2-acetic acid in 20 ml. of 0.5% ethanolic hydrogen chloride is heated under reflux. The solid gradually dissolves. After 40 min. a white crystalline solid precipitates. The solution is cooled and the solid product, ethyl 5-(p-chlorobenzyl)-3-carboxy-1,4-dimethylpyrrole-2-acetate, is filtered and dried, m.p. 197°–198°C.

EXAMPLE C

Ethyl 5-(p-chlorobenzoyl)-1,4-dimethylpyrrole-2-acetate: A 9.0 g. (0.0255 mole) sample of ethyl 5-(p-chlorobenzoyl)-3-carboxy-1,4-dimethylpyrrole-2-acetate is heated under nitrogen at 210° to 230°C. for 2 hrs. Gas is evolved. The residue is molecularly distilled in a sublimator at 195°C., 0.05 mm/Hg. The sublimate is recrystallized from cyclohexane to give ethyl 5-(p-chlorobenzoyl)-1,4-dimethylpyrrole-2-acetate as a white solid, m.p. 107°–109°C.

EXAMPLE CI 5-(p-chlorobenzoyl)-1,4-dimethylpyrrole-2-acetic acid: A suspension of 4.0 g. (0.0125 mole) of ethyl 5-(p-chlorobenzoyl)-1,4-dimethylpyrrole-2-acetate in 26 ml. of 0.5 N sodium hydroxide (0.013 mole) is heated under reflux for 30 mins. The resulting solutions is acidified with dilute hydrochloric acid, and the precipitated solid is collected by filtration, air dried and recrystallized from 2-propanol to give 5-(p-chlorobenzoyl)-1,4-dimethylpyrrole-2-acetic acid as a white crystalline solid, m.p. 178°–179°C.

Anal. Calcd. for $C_{15}H_{14}ClNO_3$: C, 61.76; H, 4.83; N, 4.82%. Found: C, 61.68; H, 4.96; N, 4.89%.

EXAMPLE CII

Ethyl 1,4-dimethyl-3-ethoxycarbonyl-5(p-toluoyl)-pyrrole-2-acetate: A solution of 30.8 g. p-toluoyl chloride and 26.6 g. (0.2 mole) of aluminum chloride in 250 ml. of 1,2-dichloroethane is added to a refluxing solution of 50.6 g. (0.2 mole) of ethyl 3-ethoxycarbonyl-1,4-dimethylpyrrole-2-acetate in 250 ml. of 1,2-dichloroethane over 30 min. The mixture is heated under reflux for 90 min. and poured into ice-diluted hydrochloric acid. The organic solution is separated, washed with brine, and dried over magnesium sulfate. The solvent is evaporated in vacuo and the residue is recrystallized from methanol to give ethyl 1,4-dimethyl-3-ethoxycarbonyl-5-(p-toluoyl)-pyrrole-2-acetate as a white solid, m.p. 108°–111°C.

EXAMPLE CIII

3-Carboxy-1,4-dimethyl-5-(p-toluoyl)-pyrrole-2-acetic acid: A suspension of 54 g. (0.145 mole) of ethyl 1,4-dimethyl-3-ethoxycarbonyl-5-(p-toluoyl)-pyrrole-2-acetate in 500 g. of 25% sodium hydroxide is heated at just below reflux for 3 hrs. The yellow suspension is then poured into ice-hydrochloric acid and the precipitated solid is collected, air dired and recrystallized from acetone-water to give 3-carboxy-1,4-dimethyl-5-(p-toluoyl)-pyrrole-2-acetic acid as a white solid, m.p. 229°–230°C.

Anal. Calcd. for $C_{17}H_{17}NO_5$: C, 64.75; H, 5.43; N, 4.44%. Found: C, 64.86; H, 5.53; N, 4.47%.

EXAMPLE CIV

Ethyl 3-carboxy-1,4-dimethyl-5-(p-toluoyl)-pyrrole-2-acetate: A solution of 37 g. (0.118 mole) of 3-carboxy-1,4-dimethyl-5-(p-toluoyl)-pyrrole-2-acetic acid in 370 ml. of ethanol containing 1.8 g. of dry hydrogen chloride is heated under reflux for 45 min. The solution is cooled and the solid which precipitated, ethyl 3-carboxy-1,4-dimethyl-5-(o-toluoyl)-pyrrole-2-acetate, is collected, m.p. 200°–202°C.

EXAMPLE CV

Ethyl 1,4-dimethyl-5-(p-toluoyl)-pyrrole-2-acetate: A solution of 33.0 g. (0.096 mole) of ethyl 3-carboxy-1,4-dimethyl-5-(p-toluoyl)-pyrrole-2-acetate in 200 ml. of quinoline with 0.1 g. copper chromite added is heated under nitrogen for 6 hr. at 200°C., then for 30 min. at 220°C. The quinoline is distilled off in vacuo. The residue is dissolved in ether and washed successively with dilute hydrochloric acid, dilute sodium hydroxide, and brine; dried over magnesium sulfate; and the solvent evaporated in vacuo to give a brown oily residue which crystallizes. It is recrystallized from methanol, sublimed at 150°C. (0.025 mm/Hg) and recrystallized from hexane to give ethyl 1,4-dimethyl-5-(p-toluoyl)-pyrrole-2-acetate as a white solid, m.p. 90°–93°C.

EXAMPLE CVI 1,4-Dimethyl-5-(p-toluoyl)-pyrrole-2-acetic acid: A suspension of 8.5 g. (0.0284 mole) of ethyl 1,4-dimethyl-5-(p-toluoyl)-pyrrole-2-acetate in 29 ml. of 1N sodium hydroxide solution is heated under reflux for 20 min. The yellow solution is diluted with water and added to dilute hydrochloric acid. The precipitated solid is collected, dried in vacuo, and recrystallized from 2-propanol to give 1,4-dimethyl-5-(p-toluoyl)-pyrrole-2-acetic acid as a white solid, m.p. 160°–161°C.

Anal. Calcd. for $C_{16}H_{17}NO_3$: C, 70.83; H, 6.32; N, 5.16%. Found: C, 70.90; H, 6.39; N, 5.25%.

EXAMPLE CVII

By following the procedure outlined in Examples XCVII through CI, except that an equivalent quantity of benzoyl chloride and 2,3,5-tribromobenzoyl chloride is employed as the starting acylating agent in place of the p-chlorobenzoyl chloride used in Example XCVII, there are obtained, as the respective products of each Example, the corresponding 5-benzoyl and 5-(2,3,5-tribromobenzoyl) derivatives.

EXAMPLE CVIII

Lower alkyl esters of the acids obtained in Examples LXXXIX, XCI, XCIII, CI, CVI and CVII are prepared by standard esterification techniques using an appropriate lower alkanol. Typical of such esters are the following products:
ethyl 1-methyl-5-(2-thenoyl)-pyrrole-2-acetate;
ethyl 1-methyl-5-(5-methyl-2-thenoyl)-pyrrole-2-acetate;
ethyl 1-methyl-5-(p-trifluoromethylbenzoyl)-pyrrole-2-acetate;
n-propyl 5-(p-chlorobenzoyl-1,4-dimethylpyrrole-2-acetate;
n-butyl 5-(p-toluoyl)-1,4-dimethylpyrrole-2-acetate;
ethyl 5-benzoyl-1,4-dimethylpyrrole-2-acetate;
isopropyl 5-(p-ethoxybenzoyl)-1,4-dimethylpyrrole-2-acetate;
ethyl 5-(2-dimethoxybenzoyl)-1,4-dimethylpyrrole-2-acetate; and
isobutyl 5-(2,3,5-tribromobenzoyl)-1,4-dimethylpyrrole-2-acetate.

EXAMPLE CIX

Primary, secondary and tertiary amides of the acids obtained in Example LXXXIX, XCI, XCIII, CI, CVI and CVII are prepared by conventional procedures, for example, by treatment with thinoyl chloride and then reacting the thus-obtained acid chloride with either ammonia, a primary lower alkylamine or a secondary lower alkylamine. Typical of such amides are the following products:
1-methyl-5-(2-thenoyl)-pyrrole-2-acetamide;
1-methyl-5-(5-methyl-2-thenoyl)-N-ethyl-pyrrole-2-acetamide;
1-methyl-5-(p-trifluoromethylbenzoyl)-pyrrole-2-acetamide;
5-(p-chlorobenzoyl)-1,4-dimethylpyrrole-2-acetamide;
5-(p-chlorobenzoyl)-N-methyl-1,4-dimethylpyrrole-2-acetamide;
5-(p-toluoyl)-1,4-dimethylpyrrole-2-acetamide;
5-(p-toluoyl)-N,N-diethyl-1,4-dimethylpyrrole-2-acetamide
5-benzoyl-N-propyl-1,4-dimethylpyrrole-2-acetamide;
5-(p-ethoxybenzoyl)-N,N-dimethyl-1,4-dimethylpyrrole-2-acetamide; and
5-(2,3,5-tribromobenzoyl)-1,4-dimethylpyrrole-2-acetamide.

EXAMPLE CX

A. 1-Chloro-2-butanone: Chlorination of methylethylketone is carried out according to Bruylant and Houssiau [Bull. Soc. Chem. Bleg., 6, 492 (1952)]. The mixture obtained is fractionally distilled at atmospheric pressure through a Vigreaux column. The fraction boiling at 135°–144°C. is shown by vapor phase chromatography to contain approximately 75% 1-chloro-2-butanone and 25% 3-chloro-2-butanone. This fraction may be used in the next example without further separation.

B. According to the procedure described by Bruylant and Houssiau (see above), chlorination of an appropriate methyl loweralkyl ketone followed by fraction distillation yields the corresponding chloromethyl loweralkyl ketones of formula (XXIV), such as, for example, chloromethyl n-butyl ketone derived from 2-hexanone.

EXAMPLE CXI

Ethyl 3-ethoxycarbonyl-4-ethyl-1-methylpyrrole-2-acetate: A 900 ml. solution of 25% aqueous methylamine is cooled in an ice bath and 101 g. (0.5 mole) of diethyl acetone decarboxylate is added. To the mixture is added 110 g. of the 1-chloro-2-butanone obtained in Example CX. Intermittant cooling is applied to keep the temperature below 60°C. The mixture is stirred for one hour and poured into ice-hydrochloric acid. The crystalline product is collected by filtration and recrystallized from methanol to yield ethyl 3-ethoxycarbonyl-4-ethyl-1-methylpyrrole-2-acetate as in a white solid, m.p. 65°–67°C.

EXAMPLE CXII

Ethyl (5-p-chlorobenzoyl)3-ethoxycarbonyl-4-ethyl-1-methylpyrrole-2-acetate: A solution of 13.8 g. (0.0788 mole) of p-chlorobenzoyl chloride and 10.5 g. (0.0788 mole) of aluminum chloride in 120 ml. of 1,2-dichloroethane is added to a refluxing solution of 21.8 g. (0.0788 mole) of ethyl 3-ethoxycarbonyl-4-ethyl-1-methylpyrrole-2-acetate. The mixture is heated unde reflux for 10 hrs. and stirred at room temperature for an additional 10 hrs. It is then poured into ice-hydrochloric acid. The organic layer is separated and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residual red oily residue crystallizes on standing. It is recrystallized twice from methanol to give ethyl (5-chlorobenzoyl)-3-ethoxycarbonyl-4-ethyl-1-methylpyrrole-2-acetate as a white solid, m.p. 72°–74°C.

EXAMPLE CXIII

3-Carboxy-5-(p-chlorobenzoyl)-4-ethyl-1-methylpyrrole-2-acetic acid: A suspension of 18.2 g. (0.044 mole) of ethyl 5-(p-chlorobenzoyl)-3-ethoxycarbonyl-4-ethyl-1-methylpyrrole-2-acetate in 170 ml. of 25% aqueous sodium hydroxide solution is heated under reflux for 3 hrs. It is cooled, diluted with water and acidified with dilute hydrochloric acid, The precipitated solid is collected by filtration and air dired. It is recrystallized from acetone-water to give 3-carboxy-5-(p-chlorobenzoyl)-4-ethyl-1-methylpyrrole-2-acetate acid, m.p. 211°–212.5°C.

EXAMPLE CXIV

Ethyl 3-carboxy-5-(p-chlorobenzoyl)-4-ethyl-1-methylpyrrole-2-acetate: A solution of 13.8 g. (0.0375 mole) of 3-carboxy-5-(p-chlorobenzoyl)-4-ethyl-1-methylpyrrole-2-acetic acid in 140 ml. of 0.5% ethanolic hydrogen chloride is heated under reflux for 45 min. After cooling, the precipitated solid is collected. A second crop is obtained by partial evaporation of the solvent, recrystallized from ethanol and combined with the first crop to give ethyl 3-carboxy-5(p-chlorobenzoyl)-4-ethyl-1-methylpyrrole-2-acetate, m.p. 184–186°C.

EXAMPLE CXV

Ethyl 5-(p-chlorobenzoyl)-4-ethyl-1-methylpyrrole-2-acetate: A 13.7 g. (0.035 mole) sample of ethyl 3-carboxy-5-(p-chlorobenzoyl)-4-ethyl-1-methypyrrole-2-acetate is heated at 200° to 210°C. under nitrogen for 90 min. The resulting oil is molecularly distilled at 185°C. and 0.1 mm pressure to yield a solid which is recrystallized from cyclohexane and then methanol to give ethyl 5-(p-chlorobenzoyl)-4-ethyl-1-methylpyrrole-2-acetate as a white solid, m.p. 73°–75°C.

EXAMPLE CXVI

EXAMPLE CXVI 5-(p-Chlorobenzoyl)-4-ethyl-1-methylpyrrole-2-acetic acid: A suspension of 4.5 g. (0.0136 mole) of ethyl 5-(p-chlorobenzoyl)-4-ethyl-1methylpyrrole-2-acetate in 28 ml. 0.5 N sodium hydroxide and 1 ml. of ethanol is heated under reflux for 30 min. The mixture is then poured into ice-dilute hydrochloric acid. The precipitated solid is filtered, air dried and recrystallized from 2-propanol to give 5-(p-chlorobenzoyl)-4-ethyl-1-methylpyrrole-2-acetic acid as a white solid, m.p. 129°–131°C.

Anal. Calcd. for $C_{16}H_{16}ClNO_3$: C, 62.85; H, 5.29; N, 4.5%. Found: C, 62.58; H, 5.40; N, 4.83%.

EXAMPLE CXVII

By following the procedures outlined in Examples CXII through CXVI, except that an equivalent quantity of benzoyl chloride and 2,3,5-tribromobenzoyl chloride is employed as the staring acylating agent in place of the p-chlorobenzoyl chloride used in Example CXII, there are obtained, as the respective products of each Example, the corresponding 5-benzoyl and 5-(2,3,5-tribromobenzoyl) derivatives.

EXAMPLE CXVIII

Ethyl 5-(p-chlorobenzoyl)-1,4,α-trimethylpyrrole-2-acetate: 6.4 Grams (0.02 mole) of ethyl 5-(p-chlorobenzoyl)-1,4-dimethylpyrrole-2-acetate is dissolved in 100 ml. of dimethyl sulfoxide (DMSO) and added to a slurry of 0.48 g. (0.02 mole) of sodium hydride in approximately 30 ml. of DMSO. The mixture is stirred for 30 mins. before 2.84 g. (0.02 mole) of methyl iodide is added. Stirring is continued for 15 mins. The reaction mixture is then poured into water and the precipitate filtered off and recrystallized from 2-propanol to yield ethyl 5-(p-chlorobenzoyl)-1,4,α-trimethylpyrrole-2-acetate, m.p. 88°–90°C.

EXAMPLE CXIX 5-(p-Chlorobenzoyl)-1,4,α-trimethylpyrrole-2-acetic acid: An ethanol solution of 2.9 g. (0.0087 mole) of ethyl 5-(p-chlorobenzoyl)1,4,α-trimethylpyrrole-2-acetate is added to 17.5 ml. 0.5 N sodium hydroxide solution and the mixture is heated under reflux for one hour. The ethanol is evaporated in vacuo and the solution poured into dilute hydrochloric acid. The precipitated solid is collected by filtration and recrystallized from ether-cyclohexane to give 5-(p-chlorobenzoyl)-1,4,α-trimethylpyrrole-2-acetic acid as a white solid, m.p. 153°–154°C. Anal. Calcd. for $C_{16}H_{16}ClNO_3$: C, 62.85; H, 5.29; N, 4.58%.

Found: C, 62.74; H, 5.22; N, 4.47%.

EXAMPLE CXX

A. The methylation procedure of Example CXVIII is repeated, except that an equivalent quantity of each ester obtained from Examples CV, CVIII and CXV is methylated instead of the ethyl 5-(p-chlorobenzoyl)-1,4-dimethylpyrrole-2-acetate used in Example CXVIII, to yield, as respective products, the corresponding α-methyl derivative of each such ester.

B. The hydrolysis procedure of Example CXIX is followed in transforming the α-methyl esters obtained in Example CXX-A into the corresponding α-methyl acids.

C. Primary, secondary and tertiary amides of the acids obtained in Examples CXVI, CXIX and CXX-B are obtained by conventional treatment with thionyl chloride and then reacting the thus-obtained acid chloride with either ammonia, a primary lower alkylamine or a secondary lower alkylamine.

EXAMPLE CXXI (−)-5-(p-Chlorobenzoyl)-1,α-dimethylpyrrole-2-acetic acid: A solution of 16.5 g. (0.057 mole) of racemic 5-(p-chlorobenzoyl)-α-methyl- 1-methylpyrrole-2-acetic acid and 6.8 g. (0.057 mole) of (+)-α-methylbenzylamine in 95% ethanol deposits crystals on standing. The solid is collected and recrystallized twice from 2-propanol to give 4.4 g. of salt, m.p. 181°–182°C., the mother liquors being set aside for use as shown in Example CXXII. The salt is partitioned between ether and 3N hydrochloric acid. The ether layer is washed with dilute hydrochloric acid and brine and dried over magnesium sulfate. The solvent is evaporated in vacuo. The solid residue is dissolved in hot ether and methylcyclohexane is added. The ether is allowed to evaporate and the precipitated solid, (−)-5-(p-chlorobenzoyl)-1,α-dimethylpyrrole-2-acetic acid, is collected by filtration: (13% yield), m.p. 106°–107°C.

EXAMPLE CXXII (+)-5-(p-Chlorobenzoyl-1,α-dimethylpyrrole-2-acetic acid: The mother liquors set aside in Example CXXI are evaporated to dryness. The residue is acidified with 3N hydrochloric acid and the precipitated acid is extracted into ether. The ether solution is then extracted with saturated sodium bicarbonate solution. The latter is acidified with dilute HCl and the precipitated solid is extracted into ether. The ether solution is washed with brine, dried over anhydrous magnesium sulfate and evaporated to dryness to yield 5-(p-chlorobenzoyl)-α-methyl-1-methylpyrrole- 2-acetic acid [presumably rich in the (:) enanthiomorph] as a yellow solid. A 14.8 g. sample is dissolved in ethanol. To the solution is added 6.15 g. (.051 mole) of (−)-α-methylbenzylamine. A crystalline salt precipitates on standing which is collected and recrystallized three times from 2-propanol to give about 6.6 g. of white crystals, m.p. 175°–177°C. The salt is partitioned between ether and 3N HCl solution. The ether layer is washed with dilute HCl and brine and dried over magnesium sulfate. The solvent is partially evaporated in vacuo and methylcyclohexane is added. The ether is allowed to evaporate at room temperature and the precipitate is collected. It is recrystallized once more in the same manner to give about 3.1 g. (21% yield) of (+)-5-(p-chlorobenzoyl)-1,α-dimethylpyrrole-2-acetic acid as a white solid, m.p. 105.5°–106.5°C.

EXAMPLE CXXIII

3-Carboxy-1,4-dimethylpyrrole-2-acetic acid: A mixture of 176 g. (0.7 mole) of ethyl 1,4-dimethyl-3-ethoxycarbonylpyrrole-2-acetate and 1760 ml. of 25% sodium hydroxide solution is heated under reflux for 3 hr. and then cooled and acidified with dilute hydrochloric acid. The precipitated solid is filtered and air dried. There is obtained 130 g. (98% yield) of 3-carboxy-1,4-dimethylpyrrole-2-acetic acid as a gray solid, m.p. 220°–222°C.

EXAMPLE CXXIV

Ethyl 3-carboxy-1,4-dimethylpyrrole-2-acetate: A solution of 130 g. (0.66 mole) of 3-carboxy-1,4-dimethylpyrrole-2-acetic acid in 1300 ml. of 0.5% ethanolic hydrogen chloride is heated under reflux for 45 min. and then filtered while hot. A white solid, ethyl 3-carboxy-1,4-dimethylpyrrole-2-acetate, precipitates from the filtrate on cooling, m.p. 182°–185°C.

EXAMPLE CXXV

Ethyl 1,4-dimethylpyrrole-2-acetate: A 70.0 g. sample (0.31 mole) of ethyl 3-carboxy-1,4-dimethylpyrrole-2-acetate is heated under nitrogen at 190°–210°C. until gas evolution ceases. The resulting yellow liquid is distilled at 82°–90°C. at 0.25 mm. to give about 41 g. (73% yield) of a clear colorless liquid, ethyl 1,4-dimethylpyrrole-2-acetate.

EXAMPLE CXXVI

Ethyl 1,4-dimethyl-5-(p-fluorobenzoyl)-pyrrole-2-acetate: A solution of 3.95 g. (0.025 mole) of p-fluorobenzoyl chloride and 3.32 g. (0.025 mole) of aluminum chloride in 20 ml. of 1,2-dichloroethane is added dropwise to a solution of 4.52 g. (0.025 mole) of ethyl 1,4-dimethylpyrrole-2-acetate in 20 ml. of 1,2-dichloroethane at room temperature. The reaction mixture is stirred for 2 hrs. and then cooled and poured into ice-dilute HCl. The organic phase is separated and washed successively with N,N-dimethyl-1,3-propanediamine, dilute hydrochloric acid and a saturated solution of sodium chloride; dried over anhydrous magnesium sulfate; and the solvent evaporated. The residue is triturated with hot hexane and crystals form upon cooling. There is obtained about 1.9 g. (25% yield) of ethyl 1,4-dimethyl-5-(p-fluorobenzoyl)-pyrrole-2-acetate as a white solid, m.p. 84°–86°C. Upon recrystallization from methanol, the m.p. is 87°–89°C.

EXAMPLE CXXVII 1,4-Dimethyl-5-(p-fluorobenzoyl)-pyrrole-2-acetic acid: A suspension of 3.03 g. (0.01 mole) of ethyl 1,4-dimethyl-5-(p-fluorobenzoyl)-pyrrole-2-acetate in 11 ml. of 1N sodium hyroxide solution is heated under reflux for 30 min. The solution is filtered while hot and acidified with dilute hydrochloric acid. The precipitate is collected, air dried and recrystallised from 2-propanol to give about 2.5 g. (91% yield) of 1,4-dimethyl-5-(p-fluorobenzoyl)-pyrrole-2-acetic acid as a white solid, m.p. 176°–178°C.

EXAMPLE CXXVIII

A. The Friedel-Crafts acylation procedure of Example CXXVI is followed except that an equivalent quantity of an appropriate aroyl chloride is substituted for the p-fluorobenzoyl chloride used therein to yield, as respective products:

ethyl 5-(p-chlorobenzoyl)-1,4-dimethylpyrrole-2-acetate, m.p. 107°–109°C;

ethyl 5-(p-methylthiobenzoyl)-1,4-dimethylpyrrole-2-acetate, m.p. 106°–108°C;

ethyl 5-benzoyl-1,4-dimethyepyrrole-2-acetate, m.p. 78°–80°C;

ethyl 5-thenoyl-1,4-dimethylpyrrole-2-acetate;

ethyl 5-(5-methylthenoyl)-1,4-dimethylpyrrole-2-acetate;

ethyl 5-(p-trifluoromethylbenzoyl)-1,4-dimethylpyrrole-2-acetate;

ethyl 5-(3′,4′-dimethoxybenzoyl)-1,4-dimethylpyrrole-2-acetate;

ethyl 5-(2′,3′,5′-tribromobenzoyl)-1,4-dimethylpyrrole-2-acetate;

ethyl 5-(p-nitrobenzoyl)-1,4-dimethylpyrrole-2-acetate;

ethyl 5-(p-cyanobenzoyl)-1,4-dimethylpyrrole-2-acetate; and ethyl 5-(o-methylbenzoyl)-1,4-dimethylpyrrole-2-acetate.

B. Each of the esters of Example CXXVIII-A is hydrolyzed in accordance with the procedure of Example CXXVII to yield the corresponding 5-aroyl derivative of 1,4-dimethylpyrrole-2-acetic acid.

C. Primary, secondary and tertiary amides of the acids obtained in Example CXXVIII-B are obtained by conventional treatment with thionyl chloride and then reacting the thus-obtained and chloride with either ammonia, a primary loweralkylamine or a secondary lower alkylamine, respectively. For example, by following the procedure of Example LXIII, except that equivalent amounts of an appropriate acid of formula (I-o) and of ammonia or an appropriate alkylamine are employed as the starting materials, the following amides are obtained:

5-(p-chlorobenzoyl)-N,N-diethyl-1,4-dimethylpyrrole-2-acetamide;

5-(p-methylthiobenzoyl)-N-ethyl-1,4-dimethylpyrrole-2-acetamide;

5-benzoyl-N-isopropyl-1,4-dimethylpyrrole-2-acetamide;

5-thenoyl-N-(n-butyl)-1,4-dimethylpyrrole-2-acetamide;

5-(p-trifluoromethylbenzoyl)-N,N-diethyl-1,4-dimethylpyrrole-2-acetamide 5-(o-methylbenzoyl)-N,N-dimethyl-1,4-dimethylpyrrole-2-acetamide;

5-(p-nitrobenzoyl)-1,4-dimethylpyrrole-2-acetamide;

5-(p-nitrobenzoyl)-N-ethyl-1,4-dimethylpyrrole-2-acetamide;

5-(p-nitrobenzoyl)-N,N-dimethyl-1,4-dimethylpyrrole-2-acetamide;

5-(p-cyomobenzoyl)-1,4-dimethyl-2-acetamide; and 5-(3',4'-dimethoxybenzoyl)-1,4-dimethyl-2-acetamide.

D. By using an equivalent amount of ethyl 5-(p-nitrobenzoyl-1,4-dimethylpyrrole-2-acetate in place of 5-(p-nitrobenzoyl)-1-methylpyrrole-2-acetonitrile in the hydrogenation procedure of Example XXIV, the product, ethyl 5-(p-aminobenzoyl)-1,4-dimethylpyrrole-2-acetate is obtained. Ammonolysis of the latter ester according to standard procedures, such as the treatment with ethanolic ammonia at somewhat elevated temperatures, affords the product, 5-(p-aminobenzoyl)-1,4-dimethylpyrrole-2-acetamide.

E. By repeating the hydrolysis procedure of Example LXVIII with an equivalent amount of the ester obtained from Example CXXVIII-D in place of the ester used therein, the product, 5-(p-aminobenzoyl)-1,4-dimethylpyrrole-2-acetic acid is obtained.

EXAMPLE CXXIX

A. The methylation procedure of Example CXVIII is repeated, except that an equivalent quantity of each ester obtained in Example CXXVIII-A, other than the 5-(p-nitrobenzoyl) ester, is methylated instead of the ethyl 5-(p-chlorobenzoyl)-1,4-dimethylpyrrole-2-acetate used in Example CXVIII, to yield, as respective products, the corresponding α-methyl derivative of each such acid.

B. By following the alkylation procedure of Example CXVIII, except that an equivalent quantity of propyl iodide and hexyl iodide is substituted for the methyl iodide used therein, there are obtained, as respective products, the respective α-propyl and α-hexyl derivatives of ethyl 5-(p-chlorobenzoyl)-1,4-dimethylpyrrole-2-acetate.

C. The hydrolysis procedure of Example CXIX is followed in transforming each of the foregoing α-lower alkyl esters into the corresponding α-lower alkyl acid form.

D. Primary, secondary and tertiary amides of the α-lower alkyl acids obtained in Example CXXIX-C are obtained by conventional treatment with thionyl chloride and then reacting the thus obtained acid chloride with ammonia, a primary lower alkylamine or a secondary lower alkylamine, respectively.

EXAMPLE CXXX

A. The esterification procedure of Example LV is repeated except that an equivalent amount of the appropriate acid obtained in Examples XLIX, LI and LII is used in place of the 5-(p-chlorobenzoyl)-1-methylpyrrole-2-acetic acid employed in Example LV to yield, as respective products:

ethyl 1-benzyl-5-(p-chlorobenzoyl)-pyrrole-2-acetate;

ethyl 1-benzyl-5-benzoyl-pyrrole-2-acetate;

ethyl 1-benzyl-5-(3',4'-dimethylbenzoyl)-pyrrole-2-acetate;

ethyl 1-benzyl-5-(p-ethoxybenzoyl)-α-methyl-pyrrole-2-acetate; and ethyl 1-benzyl-5-(2',4'-dichlorobenzoyl)-α-ethyl-pyrrole-2-acetate.

B. The procedure of Example XCV-A is followed, except that an equivalent amount of each ester of this Example CXXX-A is substituted for the methyl 5-(p-chlorobenzoyl)-1-methylpyrrole-2-acetate used in Example XCV-A, to yield as respective products:

1-benzyl-5-(p-chlorobenzoyl)-N-(2-diethylaminoethyl)-pyrrole-2-acetamide;

1-benzyl-5-benzoyl-N-(2-diethylaminoethyl)-pyrrole-2-acetamide;

1-benzyl-5-(3',4'-dimethylbenzoyl)-N-(2-diethylaminoethyl)-pyrrole-2-acetamide;

1-benzyl-5-(p-ethoxybenzoyl)-α-methyl-N-(2-diethylaminoethyl)-pyrrole-2-acetamide; and 1-benzyl-5-(2',4'-dichlorobenzoyl)-α-ethyl-N-(2-diethylaminoethyl)-pyrrole-2-acetamide.

EXAMPLE CXXXI

A. By repeating the procedure of Example CXI, except that an equivalent amount of ethylamine and n-butylamine is substituted for the methylamine employed therein, there are obtained, as respective products, ethyl 3-ethoxycarbonyl-1,4-diethylpyrrole-2-acetate and ethyl 3-ethoxycarbonyl-1-butyl-4-ethylpyrrole-2-acetate.

B. Similarly, by following the procedure of Example CXI, except that an equivalent amount of chloromethyl n-butyl ketone is substituted for the 1-chloro-2-butanone used therein, ethyl 3-ethoxycarbonyl-4-butyl-1-methylpyrrole-2-acetate is obtained.

C. The procedure of Examples CXXIII through CXXV are repeated, except that an equivalent amount of each of the products obtained in paragraphs A and B of this Example is substituted for the ethyl 1,4-dimetyl-3-ethoxycarbonylpyrrole-2-acetate initially employed in Example CXXIII, to yield, as respective final products:

ethyl 1,4-diethylpyrrole-2-acetate;

ethyl 1-butyl-4-ethylpyrrole-2-acetate; and ethyl 4-butyl-1-methylpyrrole-2-acetate.

D. The Friedel-Crafts procedure of Example CXXVI is followed using an equivalent amount of the appropriate ester obtained in paragraph C of this Example and an equivalent amount of an appropriate aroyl chloride as the acylating agent to yield the following products:

ethyl 5-(p-chlorobenzoyl)-1,4-diethylpyrrole-2-acetate;

ethyl 5-(2-thenoyl)-1,4-diethylpyrrole-2-acetate;

ethyl 5-(p-methylthiobenzoyl)-1-butyl-4-ethylpyrrole-2-acetate;

ethyl 5-(p-trifluoromethylbenzoyl)-1-butyl-4-ethylpyrrole-2-acetate;

ethyl 5-(p-nitrobenzoyl)-4-butyl-1-methylpyrrole-2-acetate;

ethyl 5-(p-cyanobenzoyl)-4-butyl-1-methylpyrrole-2-acetate; and ethyl 5-(3',4'-dimethoxybenzoyl)-4-butyl-1-methylpyrrole-2-acetate.

E. Each of the esters obtained in paragraph D of this Example is hydrolyzed in accordance with the procedure of Example CXXVII to yield the corresponding 5-aroyl derivatives of 1,4-dialkylpyrrole-2-acetic acid.

F. Primary, secondary and tertiary amides of the acids obtained in paragraph E of this Example are obtained by conventional treatment with thionyl chloride and then reacting the thus-obtained acid chloride with ammonia, a primary lower alkylamine or a secondary lower alkylamine, respectively.

What is claimed is:

1. The process of making a loweralkyl 5-aroyl-1-$R_4$-4-$R_5$-pyrrole-2-acetate of the formula:

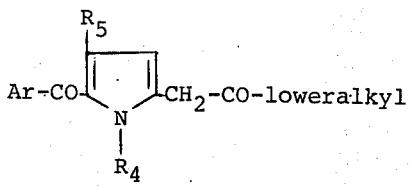

which comprises:
hydrolyzing a loweralkyl 1-$R_4$-4-$R_5$-3-loweralkoxycarbonylpyrrole-2-acetate under alkaline conditions to the di-acid, 1-$R_4$-4-$R_5$-3-carboxypyrrole-2-acetic acid, partially re-esterifying said di-acid to loweralkyl 1-$R_4$-4-$R_5$-3-carboxypyrrole-2-acetate by treating said di-acid with an acidic solution of a lower alkanol, decarboxylating the 3-carboxy group of said loweralkyl 1-$R_4$-4-$R_5$-3-carboxypyrrole-2-acetate to the pyrrole ester, loweralkyl 1-$R_4$-4-$R_5$-pyrrole-2-acetate, by heating said loweralkyl 1-$R_4$-4-$R_5$-3-carboxypyrrole-2-acetate to $CO_2$-elimination temperatures, and acylating said loweralkyl 1-$R_4$-4-$R_5$-pyrrole-2-acetate to said loweralkyl 5-aroyl-1-$R_4$-4-$R_5$-pyrrole-2-acetate by treatment with an aroyl chloride of the formula Ar-COCl in the presence of a Lewis acid in an organic solvent suitable for Friedel-Crafts acylation reactions;

wherein the foregoing said AR—CO is a member selected from the group consisting of benzoyl, thenoyl, 5-methylthenoyl, monosubstituted benzoyl, disubstituted benzoyl and trisubstituted benzoyl, each substituent of said substituted benzoyls being a member selected from the group consisting of halo, loweralkyl, trifluoromethyl, loweralkoxy, nitro, cyano and methylthio, and said $R_4$ and said $R_5$ represent loweralkyl.

2. The process of claim 1 wherein said loweralkyl 1-$R_4$-4-$R_5$-3-loweralkoxycarbonyl-pyrrole-2-acetate is ethyl 1,4-dimethyl-3-ethoxy carbonyl-pyrrole-2-acetate.

* * * * *

UNITED STATES PATENT AND TRADEMARK OFFICE
CERTIFICATE OF CORRECTION

PATENT NO. : 3,952,012
DATED : April 20, 1976
INVENTOR(S) : Carson, John Robert

It is certified that error appears in the above-identified patent and that said Letters Patent are hereby corrected as shown below:

In Column 1, line 64, "(lower alkyl)" should read ---
---(lower alkyl)$_2$ ----
In Column 4, line 39, para should be underlined
In Column 5, line 52, "-H-" should read "-N-"
In Column 6, (Figure 10) last drawing to right "$CH_2Ch_2$ -COOH" should read "$CH_2CH_2$-COOH"
In Column 6, line 61, "(XVXI) of formula (Ic)" should read '(XVII) of formula (I-c).''
In Column 8, line 59, "1-loweralkyl)" should read "1-loweralkyl"
In Column 9, line 29, "prodcts" should read ---products---
In Column 9, line 64, "formula (I-c)" should read ---
---formula (I-e)---
In Column 9, line 67, "amine" should read ---amino---
In Column 12, line 65, "tht" should read ---that---
In Column 13, line 68, "perenteral" should read --parenteral---

In Column 19, lines 39 & 40, "5-(3¦-4'" should read "5-(3',4'"
In Column 21, line 29, "p-nitrobenzoyl)" should read "p-nitrobenzoyl"
In Column 21, line 38, "2N" should read ---3N---
In Column 21, line 65, "/N" should read ---1N---
In Column 23, line 65, "Nah" should read ---NaH---
In Column 25, line 2, "XXXXVI" should read ---XXXVI---
In Column 25, line 31, "methyl--" should read "methyl-1-"
In Column 25, line 36, "Example XXXXIX" should read
---Example XXXIX---
In Column 26, line 13, "precedure" should read --procedure--
In Column 28, line 22, "4.65" should read ---4.56---

UNITED STATES PATENT AND TRADEMARK OFFICE
CERTIFICATE OF CORRECTION

PATENT NO. : 3,952,012
DATED : April 20, 1976
INVENTOR(S) : Carson, John Robert

It is certified that error appears in the above-identified patent and that said Letters Patent are hereby corrected as shown below:

In Column 31, line 7, "253°λ" should read "253°"
In Column 31, line 21, "toluoyl)1-" should read "toluoyl)-1-"
In Column 31, line 56, "$C_{16}H_{17}ClN_2O_2$: C, 6305; H, 5.62; N, 9.20%.
    Found: C,63.06; H. 5.61; N, 9.14%."
    Should read
"$C_{18}H_{21}ClN_2O_2$: C, 64.96; H, 6.36; N, 8.41%.
    Found: C, 65.02; H, 6.38; N, 8.20%."
In Column 35, line 25, "acid." should read "acid,"
In Column 35, line 56, "‐3acetate" should read "-3-acetate"
In Column 38, line 44, "benzeneether" should read "benzene-ether"
In Column 39, line 13, "yield)." should read "yield),"
In Column 39, line 29, "wite" should read "white"
In Column 39, line 52, "compoundbearing" should read
    "compound-bearing"
In Column 39, line 55, "methaol" should read ---methanol---
In Column 40, line 54, "2-acetic - acid," should read
    "2-acetic acid,"
In Column 40, line 58, "H 5.62%" should read "N 5.62%"
In Column 40, line 60, "EXAMPLe XC" should read "EXAMPLE XC"
In Column 41, line 19, " precipitate 1-" should read
    "precipitate, 1-"
In Column 41, line 28, "2acetonitrile:" should read
    "2-acetonitrile:"
In Column 41, line 41, "other" should read ---ether---
In Column 41, line 43, "Enrlich's" should read "Ehrlich's"
In Column 41, line 46, "in purified" should read "is purified"
In Column 41, line 51, "2acetic acid:" should read "2-acetic acid:"

UNITED STATES PATENT AND TRADEMARK OFFICE
CERTIFICATE OF CORRECTION

PATENT NO. : 3,952,012
DATED : April 20, 1976
INVENTOR(S) : Carson

It is certified that error appears in the above-identified patent and that said Letters Patent are hereby corrected as shown below:

```
In Column 42, line 14, "cid" should read "acid"
In Column 43, line 10, "-2acetamide;" should read "-2-acetamide;"
In Column 43, line 35, "-3ethoxycar-" should read
                            "-3-ethoxycar-"
In Column 43, line 39, "-3ethoxycarbonylpyrrole" should read
                            "-3-ethoxycarbonylpyrrole"
In Column 43, line 66, "1,4dimethyl-" should read
                            "1,4-dimethyl-"
In Column 44, line 57, "dired" should read "dried"
In Column 45, line  3, "(o-toluoyl) should read "(p-toluoyl)"
In Column 45, line 59, "chlorobenzoyl-" should read
                            "chlorobenzoyl)-"
In Column 45, line 65, "(2-dimethoxybenzoyl)" should read
                            "(2, 4-dimethoxybenzoyl)"
In Column 46, line 21, "acetamide" should read "acetamide;"
In Column 46, line 31, "Bleg." should read "Belg."
In Column 46, line 50, "butanone obtained" should read
                            "butanone mixture obtained"
In Column 46, line 56, "as in a white solid" should read
                            "as a white solid"
In Column 46, line 60, "(5-p-chlorobenzoyl)3" should read
                            "(5-p-chlorobenzoyl)-3"
In Column 46, line 67, "unde" should read "under"
In Column 47, line  9, "chlorobenzoyl" should read
                            "p-chlorobenzoyl"
In Column 47, line 19, "acid," should read "acid."
In Column 47, line 20, "dired" should read "dried"
In Column 47, line 22, "acetate" should read "acetic"
In Column 47, line 34, "-5(p-" should read "-5-(p-"
```

UNITED STATES PATENT AND TRADEMARK OFFICE
CERTIFICATE OF CORRECTION

PATENT NO. : 3,952,012
DATED : April 20, 1976
INVENTOR(S) : Carson, John Robert

It is certified that error appears in the above-identified patent and that said Letters Patent are hereby corrected as shown below:

In Column 47, line 37, "184-186°C" should read "185-186°C"
In Column 47, Line 50, EXAMPLE CXVI should only appear once
In Column 47, line 63, "4.5%." should read "4.58%."
In Column 49, line  6, "(p-Chlorobenzoyl-1" should read "(p-Chlorobenzoyl)-1"
In Column 49, line 18, "presurably" should read" presumably"
In Column 49, line 18, "(:)" should read "(+)"
In Column 49, line 18, "(:) enanthiomorph]" should read "(+)-enanthiomorph]"
In Column 50, line 23, "recrystallised" should read "recrystallized"
In Column 50, line 66, "(I-o)" should read (I-e)"
In Column 51, line 17, "N,N-dimethyl" should read "N,N-diethyl"

Signed and Sealed this

Ninth Day of May 1978

[SEAL]

Attest:

RUTH C. MASON
Attesting Officer

LUTRELLE F. PARKER
Acting Commissioner of Patents and Trademarks